(12) United States Patent
Benita et al.

(10) Patent No.: US 10,239,903 B2
(45) Date of Patent: Mar. 26, 2019

(54) PT (IV) DERIVATIVES AND NANOCARRIERS COMPRISING THEM

(71) Applicant: Yissum Research Development Company of the Hebrew University of Jerusalem Ltd., Jerusalem (IL)

(72) Inventors: Simon Benita, Tel Aviv (IL); Taher Nassar, Kfar Tur'an (IL); Dan Gibson, Jerusalem (IL); Aiman Abu Ammar, Baqa Algharbiya (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/308,415

(22) PCT Filed: Apr. 30, 2015

(86) PCT No.: PCT/IL2015/050448
§ 371 (c)(1),
(2) Date: Nov. 2, 2016

(87) PCT Pub. No.: WO2015/166498
PCT Pub. Date: Nov. 5, 2015

(65) Prior Publication Data
US 2017/0081352 A1   Mar. 23, 2017

Related U.S. Application Data

(60) Provisional application No. 61/987,717, filed on May 2, 2014.

(51) Int. Cl.
*C07F 15/00* (2006.01)
*A61K 9/00* (2006.01)
*A61K 9/51* (2006.01)

(52) U.S. Cl.
CPC ........ *C07F 15/0093* (2013.01); *A61K 9/0019* (2013.01); *A61K 9/5153* (2013.01)

(58) Field of Classification Search
CPC ... A61K 9/0019; A61K 9/5153; A61K 31/282
See application file for complete search history.

(56) References Cited

U.S. PATENT DOCUMENTS 5,648,384 A    7/1997  Kidani et al.
6,613,799 B1 * 9/2003  Maeda ................ C07F 15/0093
                                              424/450

FOREIGN PATENT DOCUMENTS

| WO | 2015/013565 A1 | 1/2015 | |
|----|----------------|--------|--|
| WO | 2015/013566 A1 | 1/2015 | |
| WO | 2015/058111 A1 | 4/2015 | |
| WO | WO2015058111 A1 * | 4/2015 | ............... A61K 9/51 |

OTHER PUBLICATIONS

Banerjee et al., "Nanoparticles in Cancer Chemotherapy", Progress in Molecular Biology and Translational Science, vol. 104, pp. 489-507, (2011).
Chin et al., "Tuning the Activity of Platinum(IV) Anticancer Complexes through Asymmetric Acylation", J. Med. Chem., vol. 55, pp. 7571-7582, (2012).
Database XP-002741988—Loh et al., "Reduced drug accumulation as a major mechanism of acquired resistance to cisplatin in a human ovarian carcinoma cell line: circumvention studies using novel platinum (II) adn (IV) ammine/amine complexes", British Journal of Cancer, vol. 66, No. 6, pp. 1109-1115, (1992). Abstract only.
Database XP-002741989—Zhang et al., "Characterization of difatty acid diamminoplatinum and effects of magnetic field on their anticancer activity", Huaxue Xuebao, vol. 58, No. 6, pp. 704-712, (2000). Abstract only.
Database XP-002741990—Zhang, "Physical-chemical property and anti-tumor activity of diamine-platinum saturated fatty acid complexes", Shaanxi Shifan Daxue Xuebao, Ziran Kexueban, vol. 30, No. 4, pp. 70-73, (2002). Abstract only.
Database XP-002741991—Zhang et al., "Structures, physicochemical properties and inhibiting effects of the amine stearo-platinum complexes on tumor cells", Xibei Daxue Xuebao, Ziran Kexueban, vol. 34, No. 1, p. 77-80, (2004). Abstract only.
Dieras et al., "Multicentre phase II study of oxaliplatin as a single-agent in cisplatin/carboplatin ± taxane-pretreated ovarian cancer patients", Annals of Oncology, vol. 13, pp. 258-266, (2002).
Elkas et al., "A phase I trial of oxaliplatin and topotecan in recurrent ovarian carcinoma", Gynecologic Oncology, vol. 104, pp. 422-427, (2007).
Fracasso et al., "Phase II Study of Oxaliplatin in Platinum-Resistant and Refractory Ovarian Cancer: A Gynecologic Group Study", J Clin Oncol, vol. 21, pp. 2856-2859, (2003).
Fujiyama et al., "Cisplatin incorporated in microspheres: development and fundamental studies for its clinical application", Journal of Controlled Release, vol. 89, pp. 397-408, (2003).
Galanski et al., "Carboxylation of Dihydroxoplatinum(IV) Complexes via a New Synthetic Pathway", Inorg. Chem., vol. 35, pp. 1709-1711, (1996).
Harper et al., "Advances in Platinum Chemotherapeutics", Chem. Eur. J., vol. 16, pp. 7064-7077, (2010).
Hoffmann et al., "MDR1 and ERCC1 Expression Predict Outcome of Patients with Locally Advanced Bladder Cancer Receiving Adjuvant Chemotherapy", Neoplasia, vol. 12, No. 8, pp. 628-636, (2010).
Holzer et al., "Contribution of the Major Copper Influx Transporter CTR1 to the Cellular Accumulation of Cisplatin, Carboplatin, and Oxaliplatin", Mol Pharmacol, vol. 70, No. 4, pp. 1390-1394, (2006).
Khan et al., "Synthesis and Characterization of a Series of Lipophilic Cisplatin Analogs with Piperidine as Nonleaving Amine Ligand", J. Coord. Chem., vol. 52, pp. 119-127, (2000).
Kostova, "Platinum Complexes as Anticancer Agents", Recent Patents on Anti-Cancer Drug Discovery, vol. 1, pp. 1-22, (2006).
Raymond et al., "Oxaliplatin: A review of preclinical and clinical studies", Annals of Oncology, vol. 9, pp. 1053-1071, (1998).

(Continued)

*Primary Examiner* — Pancham Bakshi
(74) *Attorney, Agent, or Firm* — Vorys, Sater, Seymour and Pease LLP

(57) ABSTRACT

Provided are Pt (IV) lipophilic derivatives for improved drug performance in cancer therapy, as well as nanocarriers including the same.

8 Claims, 29 Drawing Sheets

(56) References Cited

OTHER PUBLICATIONS

Seetharamu et al., "Phase II Study of Liposomal Cisplatin (SPI-77) in Platinum-sensitive Recurrences of Ovarian Cancer", Anticancer Research, vol. 30, pp. 541-546, (2010).
Siegel et al., "Cancer Statistics, 2013", CA Cancer J Clin, vol. 63, pp. 11-30, (2013).
Stathopoulos et al., "Liposomal Oxaliplatin in the Treatment of Advanced Cancer: A Phase I Study", Anticancer Research, vol. 26, pp. 1489-1494, (2006).
Sundar et al., "Phase II trial of Oxaliplatin and 5-Fluorouracil/ Leucovorin combination in epithelial ovarian carcinoma relapsing within 2 years of platinum-based therapy", Gynecologic Oncology, vol. 94, pp. 502-508, (2004).
Wexselblatt et al., "What do we know about the reduction of Pt(IV) pro-drugs?", Journal of Inorganic Biochemistry, vol. 117, pp. 220-229, (2012).
Wexselblatt et al., "Platinum(IV) Prodrugs with Haloacetato Ligands in the Axial Positions can Undergo Hydrolysis under Biologically Relevant Conditions", Angew. Chem. Int. Ed., vol. 52, pp. 6059-6062, (2013).
Xu et al., "Enhancing tumor cell response to chemotherapy through nanoparticle-mediated codelivery of siRNA and cisplatin prodrug", PNAS, vol. 110, No. 46, pp. 18638-18643, (2013).
Yang et al., "PEG-liposomal oxaliplatin potentialization of antitumor efficiency in a nude mouse tumor-xenograft model of colorectal carcinoma", Oncology Reports, vol. 25, pp. 1621-1628, (2011).
Yuan et al., "Vascular Permeability in a Human Tumor Xenograft: Molecular Size Dependence and Cutoff Size", Cancer Research, vol. 55, pp. 3752-3756, (1995).
Zhang et al., "Pt(IV) analogs of oxaliplatin that do not follow the expected correlation between electrochemical reduction potential and rate of reduction by ascorbate", Chem. Commun., vol. 48, pp. 847-849, (2012).
Zhang et al., "Facile Preparation of Mono-, Di- and Mixed-Carboxylato Platinum(IV) Complexes for Versatile Anticancer Prodrug Design", Chem. Eur. J., vol. 19, pp. 1672-1676, (2013).
Loh et al., "Reduced drug accumulation as a major mechanism of acquired resistance to cisplatin in a human ovarian carcinoma cell line: circumvention studies using novel platinum (II) and (IV) ammine/amine complexes", Br. J. Cancer, vol. 66, pp. 1109-1115, (1992).
Zhang et al., "Characterization of Difatty Acid Diamminoplatinum and Effects of Magnetic Field on Their Anticancer Activity", Acta Chimica Sinica, vol. 58, No. 6, pp. 704-712, (2000).

\* cited by examiner

PT (IV) DERIVATIVES AND NANOCARRIERS COMPRISING THEM

TECHNOLOGICAL FIELD

The present invention concerns Pt (IV) lipophilic derivatives for improved drug performance in cancer therapy and demonstrating lower toxicity, as well as nanocarriers comprising them.

BACKGROUND ART

[1] Siegel R, Naishadham D, Jemal A. *Cancer Journal for Clinicians* 2013, 63(1):11-30
[2] Sundar S, Symond R P, Decatris M P, Kumar D M, Osman A, Vasanthan S, O'byrne K J. *Gynecologic Oncology* 2004, 94, 502-508
[3] Harper B, Krause-Heuer A, Grant M, Manohar M, Garbutcheon-Singh B, Aldrich-Wright J. *Chemistry: A European Journal* 2010, 16, 7064-7077
[4] Raymond E, Chaney S G, Taamma A, Cvitkovic E. *Ann Oncol* 1998, 9(10), 1053-71
[5] Dieras V, Bougnoux P, Petit T, Chollet P, Beuzeboc P, Borel C, et al. *Ann Oncol* 2002, 13, 258-66
[6] Fracasso P M, Blessing J A, Morgan M A, Sood A K, Hoffman J S. *J Clin Oncol* 2003, 21, 2856-9
[7] Elkas J C, Winter W E 3rd, Chernofsky M R, Sunde J, Bidus M A, Bernstein S, Rose G S. *Gynecol Oncol* 2007, 104(2), 422-7
[8] Kostova I. *Recent Pat Anticancer Drug Discov* 2006, 1(1), 1-22
[9] Hoffmann A-C, Wild P, Leicht C, Bertz S, Danenberg K D, Danenberg P V, et al. *Neoplasia* 2010, 12(8), 628-36
[10] Holzer A K, Manorek G H, Howell S B. *Molecular Pharmacology* 2006, 70(4), 1390-4
[11] Banerjee D, Sengupta S. *Prog Mol Biol Transl Sci* 2011, 104, 489-507
[12] Yuan F, Dellian M, Fukumura D, Leunig M, Berk D A, *Cancer Res* 1995, 55, 3752-6
[13] Fujiyama J et al. *J Control Release* 2003, 89, 397-408
[14] Seetharamu N, Kim E, Hochster H, Martin F and Muggia F. *Anticancer Res* 2010, 30, 541-5
[15] Stathopoulos G P, Boulikas T, Kourvetaris A and Stathopoulos J., *Anticancer Res* 2006, 26, 1489-93
[16] Yang C, Liu H Z, Lu W D and Fu Z X., *Oncol Rep* 2011, 25, 1621-8.

BACKGROUND

Cancer is a major public health problem which is considered the second leading cause of death in the United States, exceeded only by heart disease, and accounts for one in four deaths in the world. Ovarian cancer ranked the most common cause of death of cancer; mainly among gynecologic malignancies in developed countries [1]. In 2014, approximately 21,980 women will be diagnosed with ovarian carcinoma in the United States and roughly 14,270 will die from this disease. Most women newly diagnosed with ovarian cancer have metastatic disease, which has a cure rate of only 15 to 20%. This phenomenon is mainly due to the lack of specific symptoms until disease has spread beyond the ovaries, at which time the chance of cure is dramatically reduced [2].

The approved platinum(II)-based anticancer agents cisplatin, carboplatin and oxaliplatin are routinely used in clinical practice for treatment of various solid tumors including ovarian cancer. It is estimated that as many as 50-70% of cancer patients are treated with a platinum drug [3]. Oxaliplatin, a third generation platinum drug, is 1,2-diaminocyclohexane (DACH) derivative of cisplatin which exhibiting several unique properties as compared to the parental compound. It is able to cause bulky DNA inter- and intrastrand adducts and conformational distortions, which prevent the binding of the mismatch repair protein complex and lead to apoptosis [4]. Oxaliplatin has demonstrated activity in platinum-sensitive and platinum-resistant ovarian cancer as a single-agent therapy in phases I and II trials [5-7]. However, the therapeutic outcome of platinum-based chemotherapy can be impaired by intrinsic or acquired resistance [8] which is one of the major limitations of platinum anticancer chemotherapy and it is the consequence of multifactorial events. Until now, several involved mechanisms have been identified. Among those, reduced drug accumulation is the most frequently observed phenomenon in platinum-resistant cell lines, which may be due to increased efflux, reduced influx or both [9-10].

In order to overcome drug drawbacks and to enhance cytotoxicity in sensitive and resistant cell lines, a great deal of efforts is being invested in the design of novel targeted carriers for platinum (II) complexes. Some research groups have added molecular tags to platinum(II) centers with the aim of increasing the targeting ability or decreasing reactivity, while others have focused on molecules containing platinum(IV) centers.

Platinum(IV) complexes have many advantages over platinum(II), including a lower toxicity profile, an increased kinetic inertness and reduced activity. They are classic examples of prodrugs, whereby a sufficiently stable and inert complex can be transported around the body until it reaches the desired target, where it can be converted to its active cytotoxic form, which in this case is platinum(II). Increasing lipophilicity of platinum drugs has emerged as a promising strategy to overcome their toxicity and cellular resistance. Lipophilic drugs enter into the cells by passive diffusion and can thereby bypass active transporters; moreover, such drugs can be administered orally rather than intravenously and show high carrier capacity. These properties allow the improvement of drug bioavailability, overcoming drug resistance, and the reduction of frequency of drug administration.

Recently, nanoparticulate therapeutic agents have shown several advantages over traditional small-molecule agents; these advantages include high agent loading, tunable size, tailored surface properties, controllable drug release kinetics, and improved pharmacokinetics. Nanoscale drug delivery vehicles have been extensively studied as carriers for bioactive compounds and several nanocarriers for cancer chemotherapeutics are already in the clinics [11]. Nanoparticles also tend to have increased accumulation in tumors as a result of the enhanced permeability and retention (EPR) effect that results from the leaky tumor neovasculatures [12]. Additionally, nanoparticles can be specifically targeted to cancer cells by surface conjugation of an appropriate ligand to further enhance the accumulation of nanoparticles in tumors. However, formulation of platinum drugs in nanoparticles has been a challenge, arising from their physicochemical properties [13]. For example, while a liposomal formulation of cisplatin was found to deliver higher levels of platinum to the tumor, it failed to exhibit clinical advantages presumably from suboptimal carrier design that required high concentrations of lipids [14]. Interestingly, there are only a few reports of nanoparticles of oxaliplatin for cancer chemotherapy. Recent preclinical and phase 1 studies with liposomal oxaliplatin have been reported and currently phase II trials are conducted, and the efficacy outcome of these studies may shed light and reveal the advantages of the formulations over free oxaliplatin [15-16].

GENERAL DESCRIPTION

The inventors of the invention disclosed herein have developed novel platinum (Pt) derivatives, with the aim of improving drug performance in cancer therapy. The invention further provides colloidal drug delivery systems, affording a higher therapeutic effect, lower toxicity and protection from in vivo metabolism.

Thus, in one of its aspects, the invention provides a compound of formula (I)

(I)

wherein
Pt is a platinum atom;
A is a $C_8$-$C_{22}$ fatty acid associated with the Pt atom via an oxygen atom of the fatty acid;
B is a $C_2$-$C_{22}$ fatty acid associated with the Pt atom via an oxygen atom of the fatty acid;
provided that each of A and B is not a $C_6$-$C_9$ branched alkyl fatty acid;
L is a ligand atom or group of atoms selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, halide atom (F, I, Br, Cl), substituted or unsubstituted amine —$NR_1R_2$, substituted or unsubstituted —$OR_3$, substituted or unsubstituted —$SR_4$, substituted or unsubstituted —$S(O)R_5$, substituted or unsubstituted alkylene-COOH, —OH, —SH, —NH, or any one of ligands L1 to L5 as designated herein; and
n is the number of ligand moieties, being 1, 2, 3, or 4;
$R_1$ and $R_2$ are each independently selected from hydrogen, alkyl, alkenyl, alkenyl, cycloalkyl, cycloalkenyl, cycloalkynyl, aryl, heteroaryl, heterocyclyl, halide, —$C(O)NR_6R_7$, sulfinyl, ester, and carbonyl; or wherein $R_1$ and $R_2$ in form a cyclic structure with the N atom they are bonded to;
each of $R_3$, $R_4$, and $R_5$ is independently selected from hydrogen, alkyl, alkenyl, alkenyl, cycloalkyl, cycloalkenyl, cycloalkynyl, aryl, heteroaryl, heterocyclyl, halide, sulfinyl, ester, and carbonyl; and
$R_6$ and $R_7$ are each independently selected from hydrogen, alkyl, alkenyl, alkenyl, cycloalkyl, cycloalkenyl, cycloalkynyl, aryl, heteroaryl, heterocyclyl, halide, sulfinyl, ester, carbonyl, —OH, —SH and —NH.

The term "fatty acid" as used herein is meant to encompass a carboxylic acid with an aliphatic tail (chain), a branched alkyl or branched aromatic-alkyl with cyclic or heterocyclic moiety of between about 1 and 22 carbon atoms, which is either saturated or unsaturated. Where the number of carbon atoms in the fatty acid is indicated, e.g., by the abbreviated form $C_{8-22}$, it should be understood that the carbonyl (C=O) atom of the fatty acid is counted as well, unless otherwise indicated.

It should be noted that within the context of the present invention, the fatty acid groups may not be a $C_6$-$C_9$ branched alkyl fatty acids. In other words, in a compound of formula (I) both A and B cannot be $C_6$-$C_9$ branched alkyl fatty acids.

Compounds of the invention may comprise 2 long fatty acids, i.e. both fatty acid A and fatty acid B may be each selected from $C_{8-22}$ fatty acids, which may be the same or different (excluding the case where both A and B are each a $C_6$-$C_9$ branched alkyl fatty acid). Alternatively, compounds of the invention may comprise at least one long fatty acid selected from $C_{8-22}$ fatty acids, being A or B, and at least one short fatty acid selected from $C_{2-7}$ fatty acids, being the other of A and B. For example, in some embodiments, A may be a long fatty acid such as a $C_8$-fatty acid, and B may be the same fatty acid, a different long fatty acid, or a short fatty acid such as $C_3$-fatty acid.

As a person of skill in the art would understand, a fatty acid having between 2 and 7 carbon atoms (e.g., $C_{2-7}$ fatty acid), when bonded via its oxygen atom to a central Pt atom in a compound of the invention, is of the general form

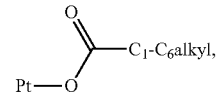

wherein the carbon atom of the carbonyl group and the C1-C6 atoms of the alkyl groups, in combination, give a $C_{2-7}$ fatty acid. Thus, the shortest fatty acid is a two-carbon fatty acid. The longest fatty acid in the above depicted fatty acid structure being a seven-carbon fatty acid.

The selection of a specific fatty acid or a combination of fatty acids to substitute Pt compounds of the invention depends inter alia on the desired lipophilicity (the compound ability to dissolve in oily substances and non-polar solvents). Thus, the selection allows tailoring of lipophilicity and thereby controlling their permeability through cellular membranes.

In some embodiments, A is selected from octanoic (caprylic) acid, nonanoic (pelargonic) acid, decanoic (capric) acid, undecanoic (undecylic) acid, dodecanoic (lauric) acid, tridecanoic (tridecylic) acid, tetradecanoic (myristic) acid, pentadecanoic (pentadecylic) acid, hexadecanoic (palmitic) acid, heptadecanoic (margaric) acid, octadecanoic (stearic) acid, nonadecanoic (nonadecylic) acid, eicosanoic (arachidic) acid, heneicosanoic (heneicosylic) acid and docosanoic (Behenic) acid.

In other embodiments, B is a $C_2$-$C_7$ fatty acid. In some embodiments, B is selected from propanoic (propionic) acid, butanoic (butyric) acid, pentanoic (valeric) acid, hexanoic (caproic) acid, and heptanoic (enanthic) acid.

Compounds of the invention may be defined as "Platinum (Pt) complexes", in which the platinum atom may be associated with a plurality of ligands and may assume different valency values. In some embodiments, the platinum atom is platinum(III), platinum(IV), platinum(V), or platinum(VI).

Each ligand atom or group (group of atoms, e.g., covalently linked) L may be associated with the Pt atom via any chemical or physical bond (linkage), such as covalent, ionic, Van der Walls or coordinative bond which holds the Pt atom and at least one of the ligand atoms together. Typically, the platinum atom is associated to the ligand(s) via coordinative bond(s). The number, n, of ligands, L, associated with the Pt atom (in the form "L(n)", integer n denotes 1, 2, 3, or 4 ligands L which are associated with the Pt atom) may also be tailored in order to modify one or more parameters of the compound. In some embodiments, n is 1. In some embodiments, n is 2. In some embodiments, n is 3. In some embodiments, n is 4.

The ligands L may be monodentate, i.e., associated via a single bond between the Pt atom and a single atom of the ligand L. The ligands L may also be polydentate ligands, having more than one atom that can associate (or link, coordinate) directly to the Pt atom in a complex. In some embodiments, the compound has at least one monodentate ligand. In some embodiments, the compound has at least one polydentate ligand. In some embodiments, the at least one polydentate ligand is a bidentate ligand. In some embodiments, the at least one polydentate ligand is a tridentate ligand. In some embodiments, the at least one polydentate ligand is a tetradentate ligand.

As compounds of the invention are Pt complexes, they may exhibit any structural isomerization, stereoisomerization or optical isomerization. In some embodiments, the compound is a cis isomer. In some embodiments, the compound is a trans isomer. In some embodiments, the compound is a mer-isomer. In some embodiments, the compound is a fac-isomer.

In some embodiments, at least one ligand L is a halide selected from F, Cl, Br, and I. In embodiments, the halide may be Cl. In some other embodiments, at least one other ligand L is an amine.

In some embodiments, the compound is of formula (II),

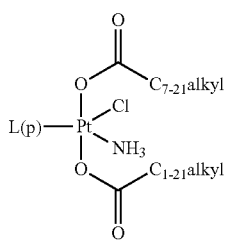

(II)

wherein L is as defined hereinabove and p is the number of ligand moieties, being 0, 1 or 2.

The terminology "L(p)" denotes the number of available attachment points for additional L ligands to Pt atom. In some embodiments, p is 0. In some embodiments, p is 1. In some embodiments, p is 2.

In other embodiments, at least one ligand L is an amine, which may be selected from ammonia, a primary amine, a secondary amine, a non-planar heterocyclic aliphatic amine or a heterocyclic aromatic amine.

According to some embodiments, the primary amine is selected from methylamine, ethylamine, n-propylamine, isopropylamine, n-butylamine, n-hexylamine, n-heptylamine and n-nonylamine.

According to other embodiments, the secondary amine is selected from dimethylamine, diethylamine, dipropylamine and dibutylamine.

According to some other embodiments, the non-planar heterocyclic aliphatic amine is selected from piperazine, 2-methylpiperazine, piperadine, 2-, 3- or 4-hydroxypiperidine, 4-piperidino-piperidine, pyrrolidine, 4-(2-hydroxyethyl)piperazine and 3-aminopyrrolidine.

According to further embodiments, the heterocyclic aromatic amine is selected from pyridine, 2-, 3-, or 4-aminopyridine, 2-, 3-, or 4-picoline, quinoline, 3-, or 4-aminoquinoline, thiazole, imidazole, 3-pyrroline, pyrazine, 2-methylpyrazine, 4-aminooquinaldine and pyridazine.

In further embodiments, n is 2, 3 or 4, and wherein at least 2 ligands L are identical. In some embodiments, L is a halide or an amine.

In some such embodiments, the compound may be selected from compounds of formulae (III) and (IV):

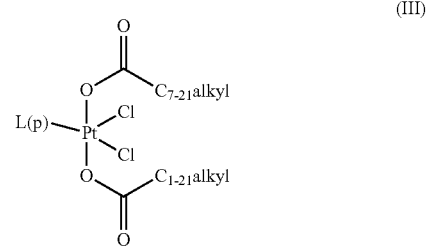

(III)

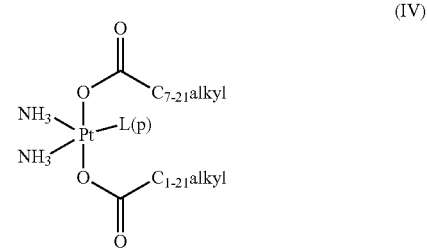

(IV)

wherein L is as defined hereinabove and p is the number of ligand moieties, being 0, 1 or 2.

In other embodiments, at least 2 ligands L are halides and the other ligands L are amines. In further embodiments, at least 2 ligands L are amines and the remainder ligands are halides.

According to some embodiments, the compound may be of formula (V) or formula (VI):

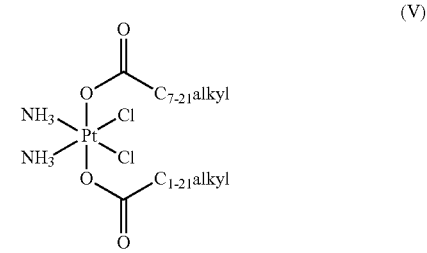

(V)

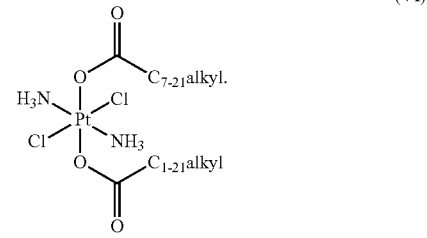

(VI)

As already noted above, the compounds of the invention comprise a fatty acid moiety A, a fatty acid moiety B, (A and B may be the same or different), and may further comprise at least one ligand L. In some embodiments, the at least one ligand L is selected from ligands designated herein L1 through L5.

L1 being the ligand:

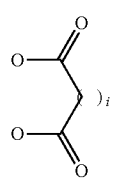
(L1)

wherein i being an integer between 0 and 5; wherein the ligand associates to the Pt via the oxygen atoms.

L2 being the ligand:

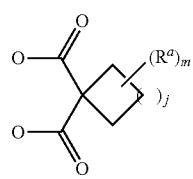
(L2)

wherein j is an integer between 0 and 2, m is an integer between 0 and 6, and $R^a$ is selected from hydrogen, substituted or unsubstituted alkyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, substituted or unsubstituted heteroaryl, substituted or unsubstituted heterocyclyl, substituted or unsubstituted alkenyl, substituted or unsubstituted alkynyl, halogen, substituted or unsubstituted —$NR_1R_2$, substituted or unsubstituted —$OR_3$, substituted or unsubstituted —$SR_4$, substituted or unsubstituted —$S(O)R_5$, substituted or unsubstituted alkylene-COOH, substituted or unsubstituted ester, OH, —SH, and —NH, phenyl, hydroxyl; wherein the ligand is associates to the Pt via the oxygen atoms. $R_1$, $R_2$, $R_3$, $R_4$ and $R_5$ are as defined hereinabove.

L3 being the ligand:

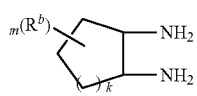
(L3)

wherein k is an integer between 0 and 2, m is an integer between 0 and 6, and $R^b$ is selected from hydrogen, substituted or unsubstituted alkyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, substituted or unsubstituted heteroaryl, substituted or unsubstituted heterocyclyl, substituted or unsubstituted alkenyl, substituted or unsubstituted alkynyl, halogen, substituted or unsubstituted —$NR_1R_2$, substituted or unsubstituted —$OR_3$, substituted or unsubstituted —$SR_4$, substituted or unsubstituted —$S(O)R_5$, substituted or unsubstituted alkylene-COOH, substituted or unsubstituted ester, OH, —SH, and —NH, phenyl, hydroxyl; wherein the ligand associates to the Pt via the amine moieties. $R_1$, $R_2$, $R_3$, $R_4$ and $R_5$ are as defined hereinabove.

L4 being the ligand:

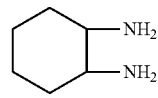

wherein the ligand associates to the Pt via the amine moieties.

L5 being the ligand:

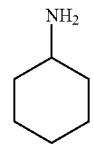

wherein the ligand associates to the Pt via the amine moiety.

In some embodiments, in a compound according to formula (I), L is L1 or L2 or L3 or L4 or L5 or any combination thereof.

In some embodiments, wherein n is larger than 1, each L is independently selected from L1 through L5.

In some embodiments, in a compound of formula (I), wherein n is larger than 1, two ligands are identical and the rest of the ligands are independently L1 or L2 or L3 or L4 or L5.

In some embodiments, at least one ligand L is L1 and the compound having the formula (VII):

(VII)

$$\text{L(p)—Pt structure with } C_{7\text{-}21}\text{alkyl and } C_{1\text{-}21}\text{alkyl}$$

wherein L is as defined hereinabove and p is the number of ligand moieties, being 0, 1 or 2.

In embodiments of a compound of formula (VII), L may be —$NR_1R_2$, wherein $R_1$ and $R_2$ are as defined herein.

In other embodiments, at least one ligand L is L4 and the compound is of the formula (VIII):

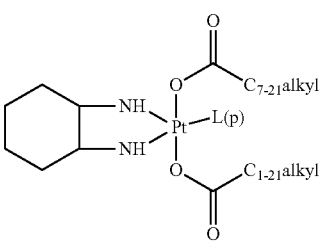
(VIII)

wherein L is as defined hereinabove and p is the number of ligand moieties, being 0, 1 or 2.

In some embodiments, n is 2, one ligand is L1 and the other ligand is L4. In such embodiments, the compound of the invention may be a compound of formula (IX):

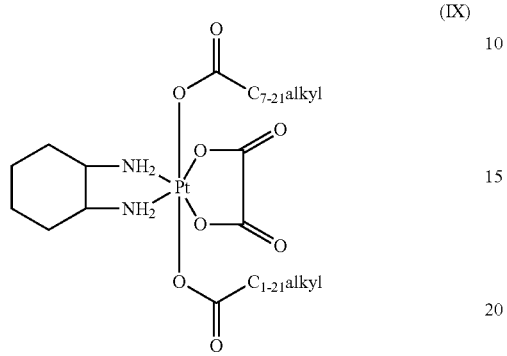
(IX)

In other embodiments, where at least one ligand is L1 or L2, at least one other ligand L is a halide or an amine.

According to some embodiments, n is 2, 3 or 4, at least one ligand is L1 and at least one other ligand is a halide or an amine.

According to other embodiments, n is 2, 3 or 4, at least one ligand is L4 and at least one other ligand is a halide or an amine.

According to additional embodiments, n is 3 or 4, at least one ligand is L1 or L4 and at least 2 of the other ligands are identical and selected from a halide and an amine.

In some embodiments, at least one ligand L is bound to the platinum atom via at least one heteroatom selected from nitrogen, oxygen and sulfur. In such embodiments, some of the bonds between the platinum atom and the heteroatom(s) may be covalent and some of the bonds may be coordinative bonds.

According to some embodiments, the compounds of the invention may be selected from:

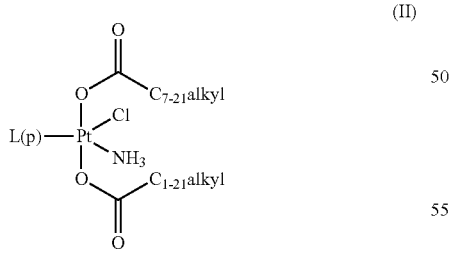
(II)

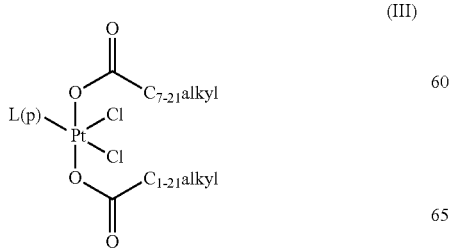
(III)

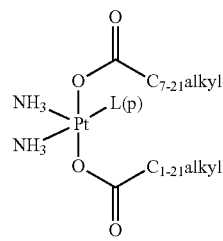
(IV)

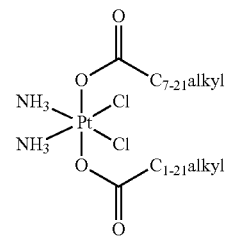
(V)

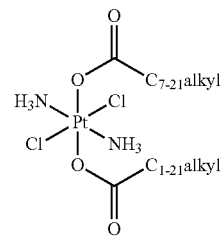
(VI)

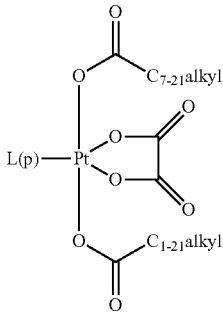
(VII)

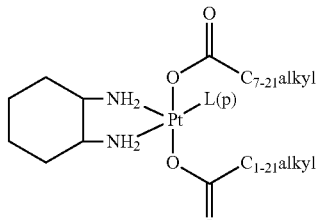
(VIII)

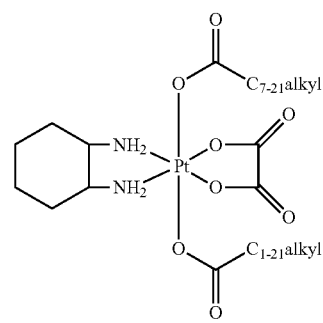
(IX)

(X)
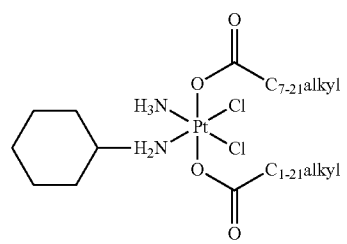
(XI)
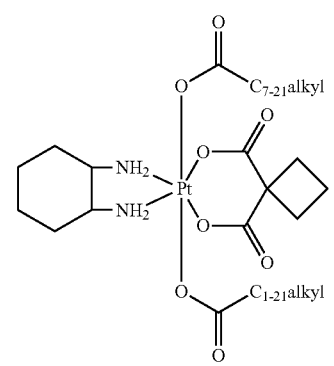
(XII)
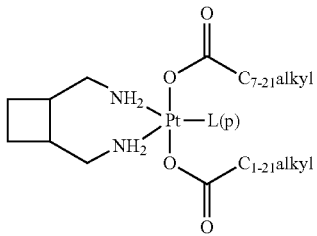
(XIII)
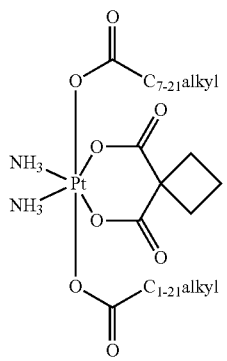
wherein, where relevant, L is as defined hereinabove and p is the number of ligand moieties, being 0, 1 or 2.
In other embodiments, the compound is of formula (Va) or (IXa), shown below, wherein the $C_{1-6}$alkyl is selected from —$C_1$alkyl, —$C_2$alkyl, —$C_3$alkyl and —$C_4$alkyl. In some embodiments, the compound is of formula (Va) or (IXa) wherein C1-6alkyl is methyl.
(Va)
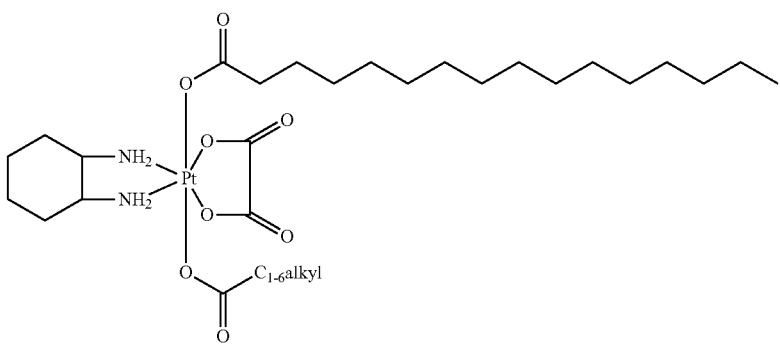
(IXa)
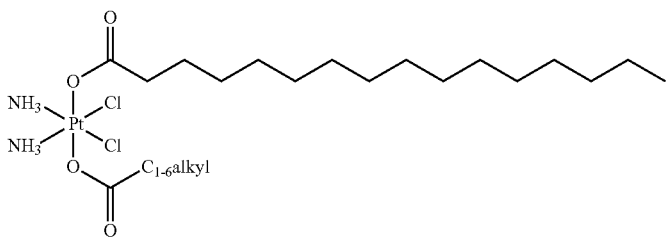

In other embodiments, the compound is of formula (Vb) or (IXb):

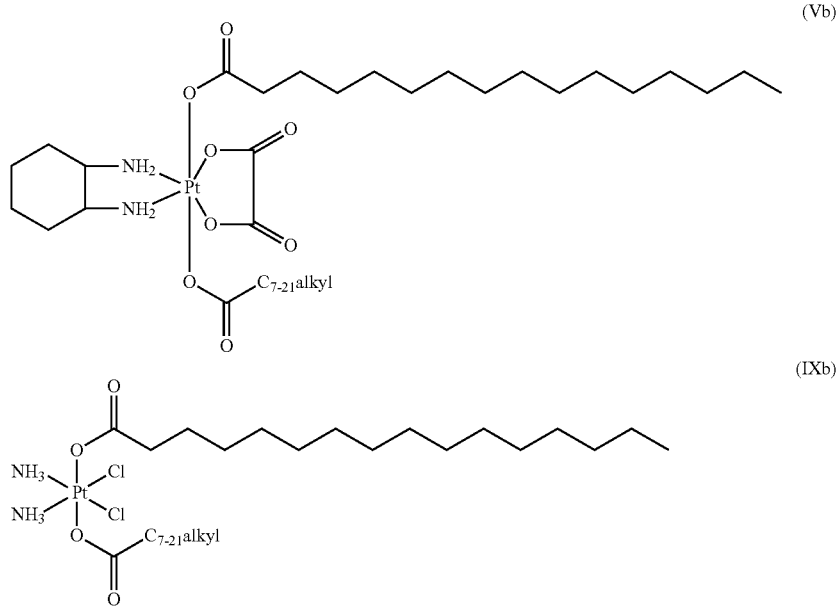

(Vb)

(IXb)

In some other embodiments, the compound is of formula (Vc) or (IXc):

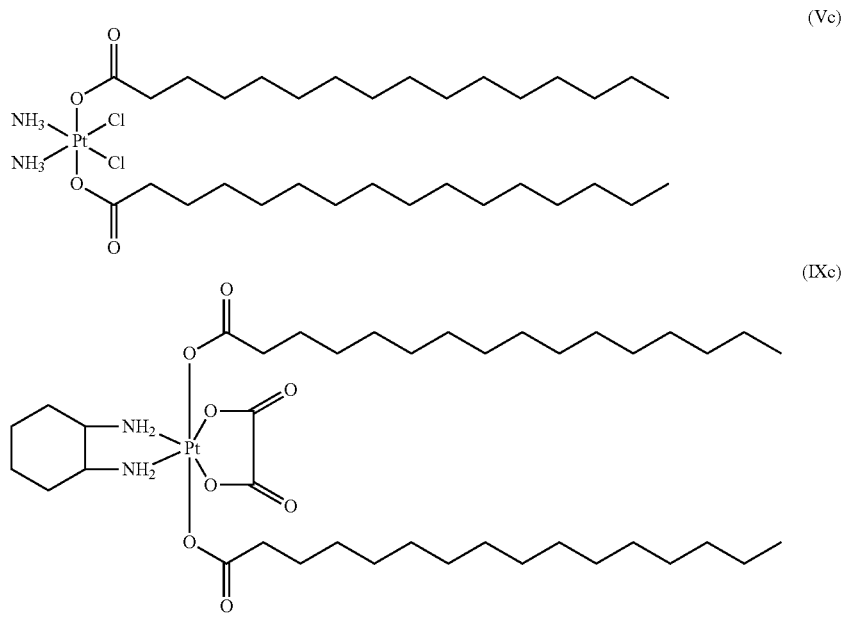

(Vc)

(IXc)

In some embodiments, the compound of the invention is Formula (Va) or (IXa) wherein the $C_{1-6}$alkyl is methyl.

In some embodiments, the compound is oxaliplatin palmitate acetate, herein referred to as OXA-PAL-ACT (OPA), being the compound designated Compound B in FIG. 1A.

Thus, the invention provides the compound of Formula (I) OXA-PAL-ACT (OPA), compositions comprising same, uses thereof and encapsulated or particulate forms thereof.

In another aspect of the invention, there is provided a compound of Formula (I) comprising a platinum atom associated to one or more $C_{8-22}$ fatty acid groups, provided that said fatty acid is not a $C_6$-$C_9$ branched alkyl fatty acid.

In yet another aspect, the invention provides a Pt-anticancer agent associated to one or more $C_{8-22}$ fatty acid groups, provided that said fatty acid is not a $C_6$-$C_9$ branched alkyl fatty acid.

In another aspect there is provided a compound comprising a platinum atom associated to one or more $C_{8-22}$ fatty acid groups, the compound having a log P value of between about 2 and 9 in octanol/water mixture, provided that said fatty acid is not a $C_6$-$C_9$ branched alkyl fatty acid.

In another aspect of the invention, there is provided a compound of Formula (I), as defined, having a log P value of at least 2 in the dual solvent system of octanol/water.

In some embodiments, the compound of the invention has a log P value of at least 7 in octanol/water solvent system. In other embodiments, the compound of the invention has a log P value of between about 2 and about 9 in octanol/water.

In other embodiments, the compound of the invention has a log P value of between about 2 and 4 in octanol/water.

It is of note that the log P value is a measure of the compound permeability through cell membranes following its injection into the blood stream, either in free drug form or incorporated in carriers.

As used herein, "alkyl", "alkenyl" and "alkynyl" carbon chains, if not specified, contain from 1 to 20 carbons, or 2 to 16 carbons, and are straight or branched. In some embodiments, the carbon chain contains 1 to 10 carbon atoms. In other embodiments, the carbon chain contains 1 to 6 carbon atoms. In some other embodiments, the carbon chain contains 2 to 6 carbon atoms. Alkenyl carbon chains of from 2 to 20 carbons, which in certain embodiments contain 1 to 8 double bonds; alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and in yet certain other embodiments, may contain 1 to 5 triple bonds.

Exemplary alkyl, alkenyl and alkynyl groups herein include, but are not limited to, methyl, ethyl, propyl, isopropyl, isobutyl, n-butyl, sec-butyl, tert-butyl, isohexyl, allyl (propenyl) and propargyl (propynyl).

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms. In other embodiments, cycloalkenyl groups contain 4 to 7 carbon atoms and cycloalkynyl groups, in yet further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "aryl" refers to aromatic monocyclic or multicyclic groups containing from 6 to 10 carbon atoms. Aryl groups include, but are not limited to, groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a saturated mono- or multi-cyclic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidine, or the nitrogen may be quaternized to form an ammonium group where the substituents are selected as above.

The term "substituted" refers to substitution on at least one atom of a ligand as defined hereinabove. In some embodiments the substituent is selected from alkyl, alkenyl, alkynyl, cycloalkyl, cycloalkenyl, cycloalkynyl, aryl, heteroaryl, heterocyclyl, halogen, —$NR_1R_2$, —$OR_3$, —$SR_4$, —$S(O)R_5$, alkylene-COOH, ester, —OH, —SH, and —NH. In some embodiments, the number of substituent (on certain ligand) is 1 or 2 or 3 or 4 or 5 or 6 or 7 or 8 or 9 or 10 substituents.

According to some embodiments, the compounds of the invention are in a salt form, typically in a pharmaceutically acceptable salt form. The term "salt form" denotes free base or free acid form, comprising a compound of the invention (i.e. charged complex), and at least one counter ion. "Pharmaceutically acceptable salt(s)", refer to salts that are safe and effective for pharmaceutical use in mammals (e.g., humans) and that possess the desired biological activity.

In some embodiments, the salt is selected from hydrochloride salt, hydrobromide salt, hydroiodide salt, nitrate salt, sulfate salt, bisulfate salt, phosphate salt, acid phosphate salt, isonicotinate salt, acetate salt, lactate salt, salicylate salt, citrate salt, tartrate salt, pantothenate salt, bitartrate salt, ascorbate salt, succinate salt, maleate salt, gentisinate salt, fumarate salt, gluconate salt, glucaronate salt, saccharate salt, formate salt, benzoate salt, glutamate salt, methanesulfonate salt, ethanesulfonate salt, benzensulfonate salt, p-toluenesulfonate salt and pamoate salt. Other anions suitable in compounds of the invention, are described, for example, in Berge et al., "Pharmaceutical Salts," *J. of Pharmaceutical Science*, 66:1-19 (1977)).

In another one of its aspects, the invention provides a nanocarrier comprising at least one compound as herein described. In some embodiments, the nanocarrier may be selected from a nanoparticle, a nanocapsule or mixtures thereof.

As used herein, the "nanocarrier" of the invention is a particulate matter, which is biocompatible and sufficiently resistant to chemical and/or physical destruction, such that a sufficient amount of the nanocarriers remain substantially intact after administration into the human or animal body and for sufficient time to be able to reach the desired target tissue (organ). Generally, the nanocarriers are spherical in shape, having an average diameter of up to 700 nm. Where the shape of the nanocarrier is not spherical, the diameter refers to the longest dimension of the nanocarrier.

Depending on various parameters associated with the compound of the invention (e.g. solubility, molecular weight, polarity, electrical charge, reactivity, chemical stability, biological activity, and others), the compound may be contained (encapsulated) in nanocapsules (NCs), and/or embedded in a matrix making-up nanoparticle (NPs). For the chosen application, the nanocarrier may therefore be in the form of core/shell (termed hereinafter also as nanocapsule), having a polymeric shell and a core containing at least one compound of the invention.

Alternatively, the nanoparticles may be of a substantially uniform composition not featuring a distinct core/shell structure. These nanocarriers are herein referred to as nanoparticles (NPs).

In some embodiments, the average diameter of the nanocarrier is between about 100 and 200 nm. In other embodiments, the average diameter is between about 200 and 300 nm. In further embodiments, the average diameter is between about 300 and 400 nm, the average diameters between about 400 and 500 nm. In further embodiments, the average diameter is between about 600 and 700 nm.

In some other embodiments, the average diameter of the nanocarrier is between about 50 and 700 nm. In other embodiments, the average diameter is between about 50 and 500 nm. In other embodiments, the average diameter is between about 50 and 400 nm. In further embodiments, the average diameter is between about 50 and 300 nm. In further embodiments, the average diameter is between about 50 and 200 nm. In further embodiments, the average diameter is between about 50 and 100 nm.

The nanocarriers may each be substantially of the same shape and/or size. In some embodiments, the nanocarriers have a distribution of diameters such that no more than 0.01 percent to 10 percent of the particles have a diameter greater than 10 percent above or below the average diameter noted above, and in some embodiments, such that no more than 0.1, 0.2, 0.4, 0.6, 0.8, 1, 2, 3, 4, 5, 6, 7, 8, or 9 percent of the nanocarriers have a diameter greater than 10 percent above or below the average diameters noted above.

Exemplary suitable materials for forming the nanocarriers, nanocapsules and/or nanoparticles, are polyesters including polylactic acid (PLA), polyglycolic acid (PGA), polyhydroxybutyrate and polycaprolactone), poly(orthoesters), polyanhydrides, polyamino acid, poly(alkyl cyanoacrylates), polyphophazenes, copolymers of (PLA/PGA) and asparate or polyethylene-oxide (PEO).

In some embodiments, the nanocarrier is a nanoparticle, said nanoparticle comprising a first matrix, wherein said at least one compound of the invention is embedded within said matrix.

In other embodiments, the nanocarrier is a nanocapsule, said nanocapsule comprising a first shell encapsulating said at least one compound of the invention or a composition comprising at least one compound of the invention.

Each of the nanocarriers may be further enveloped by another encapsulation layer, thereby forming a double-layered protection. Thus, in some embodiments, the nanocarrier is further encapsulated within a second shell layer, which may comprise the same or different material than that of the first shell layer. In other embodiments, the nanocarrier is further embedded within a second matrix, the first and second matrices may be comprised of the same or different materials.

In order to increase the amount of active compound reaching the target organ, it is sometimes desired to provide a product comprising a plurality of nanocarriers packed in a single casing. Therefore, in another aspect, there is provided a nano- or a microcapsule comprising a plurality of nanocarriers of the invention.

Another aspect provides a nano- or microparticle comprising a plurality of nanocarriers of the invention. Such nano- or microparticles may endow long-acting dosage forms when administered parenterally, or may be used as powders for oral, inhalation or pulmonary delivery of compounds of the invention.

In some embodiments, the nano- or microparticle, that comprises a plurality of nanocarriers of the invention, may be formed of a hydrophobic polymer.

In such embodiments, the plurality of nanocarriers may be (i) encapsulated by a hydrophobic cross linked protein e.g. (HSA) Human Serum Albumin (namely forming double nanoencapsulation) or (ii) embedded in a matrix, such as a matrix formed of a hydrophobic polymer blend. Such a hydrophobic polymeric blend may be an Eudragit:HPMC blend, in which the Eudragit has pH-dependent solubility, while HPMC is aqueous soluble irrespective of the pH.

In another one of its aspects, the invention provides a composition comprising a compound, a nanocarrier, a nano- or microcapsule, or a nano- or microparticle as described herein. Typically, the composition is a pharmaceutical composition.

As used herein, "pharmaceutical composition" comprises a therapeutically effective amount of a compound of the invention, together with suitable diluents, preservatives, solubilizers, emulsifiers, adjuvant and/or carriers. Such compositions are liquids or lyophilized or otherwise dried formulations and include diluents of various buffer content (e.g.; Tris-HCL, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts or nanoemulsions either negatively or positively charged. Such compositions will influence the physical state, solubility, stability, rate of in vivo release, and rate of in vivo clearance. Controlled or sustained release compositions include formulation in lipophilic depots (e.g., fatty acids, waxes, oils).

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions or self-emulsifying formulations. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers. Tablet forms can include one or more of lactose, sucrose, mannitol, corn starch, potato starch, alginic acid, microcrystalline cellulose, acacia, gelatin, guar gum, colloidal silicon dioxide, croscarmellose sodium talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include sterile nanoemulsions, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In some embodiments, the composition is suitable for oral administration.

In other embodiments, the composition is suitable for intravenous administration.

In some other embodiments, the composition is in a nanoemulsion form. The emulsions may include but not be limited to the forms O/W, W/O, W/O/W, O/W/O, W/O$_1$/O$_2$, W/O$_2$/O$_1$, O$_1$/W/O$_2$, O$_1$/O$_2$/W, O$_2$/O$_1$/W, O$_2$/W/O$_1$ and combinations of these forms with continuous or bicontinuous phases.

Another aspect of the invention provides a compound, a nanocarrier, a nano- or microcapsule, or a nano- or microparticle as described herein, for use in treating or delaying progression of a proliferative disorder.

In yet another aspect there is provided use of a compound, a nanocarrier, a nano- or microcapsule, or a nano- or microparticle as described herein, for the preparation of a medicament for treating or delaying progression of a proliferative disorder.

A further aspect of the invention provides a method for treating or delaying or preventing the progression of a proliferative disorder, the method comprising administering an effective amount of a compound, a nanocarrier, a nano- or microcapsule, or a nano- or microparticle as described herein, to a subject in need thereof.

The term "proliferative disorders" encompass diseases or disorders that effect a cellular growth, differentiation or proliferation processes. In some embodiments, the proliferation disorder is cancer. The term "cancer" as used herein encompasses any neoplastic disease which is characterized by abnormal and uncontrolled cell division causing malignant growth or tumor. Cancer as used herein may refer to either a solid tumor or tumor metastasis.

Non-limiting examples of cancer are ovary cancer, and pancreatic cancer, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Solid cancers appear in many forms, for example, breast cancer, prostate cancer, sarcomas, and skin cancer. One form of skin cancer is melanoma.

In some embodiments, the cancer is selected from lung cancer, colon cancer, pancreatic cancer and ovarian cancer.

The term "treatment" as used herein refers to the administering of a therapeutic amount of the composition of the present invention which is effective to ameliorate undesired symptoms associated with a disease, to prevent the manifestation of such symptoms before they occur, to slow down the progression of the disease (also referred to herein as "delaying the progression"), slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

The term "effective amount" as used herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

In some embodiments, the effective amount of the compound is administrated by one or more of the following routes: oral, rectal, transmucosal, transnasal, intestinal, parenteral, intramuscular, subcutaneous, intramedullary injections, intrathecal, direct intraventricular, intravenous, intraperitoneal, intranasal, or intraocular injections.

A further aspect of the invention provides a kit comprising a composition as herein described and instructions for use.

In another aspect, the invention provides a compound of the invention as a prodrug. As used herein the term "prodrug" refers to an agent which is converted into the parent drug (active agent) in vivo by some physiological chemical process (e.g., a prodrug converted to the desired drug form under physiological conditions). The prodrugs of the invention are useful as they may be easier to administer than the parent drug, they are less toxic and present improved bioavailability. After administration, the prodrug is enzymatically or chemically cleaved to deliver the active drug in the blood or tissue.

In some embodiments, the prodrug releases the active agent (activated) in a physiological pH (7.4). In some embodiments, the prodrug is activated at a pH lower than the physiological pH. In some embodiments, the prodrug is activated at a pH of about 6.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

(FIG. 4A) SE and (FIG. 4B) BSE mode.

(FIG. 8B) cytotoxic activity of oxaliplatin derivatives on BxPC-3 cell line; (FIG. 8C) cytotoxic activity of oxaliplatin derivatives on ovcar-8 cell line monolayer representing ovarian cancer; and (FIG. 8D) cytotoxic activity of oxaliplatin derivatives on SKOV-3 cell line monolayer representing ovarian cancer.

(FIG. 13A) in vitro Pt accumulation/cells after 24 h treatment SKOV-3-luc; (FIG. 13B) in vitro Pt accumulation/protein after 24 h treatment SKOV-3-luc.

(FIG. 14A) in vitro Pt accumulation/cells after 24 h treatment SKOV-3; (FIG. 14B) in vitro Pt accumulation/protein after 24 h treatment SKOV-3.

DETAILED DESCRIPTION OF EMBODIMENTS

Materials and Methods
Materials

Oxaliplatin was acquired from AK Scientific, Inc. USA. Palmitic acid, Thiazolyl Blue Tetrazolium Bromide, ethyl chloroformate and cysteine were purchased from Sigma-Aldrich. Oleic acid (Fisher Scientific) and PLGA 50 KDa, Resomer® RG 504 H (Boehringer Ingelheim lot. 1035006). Lipoid E80 (Lipoid GmbH-Germany, lot. 1031157). All organic solvents were HPLC grade and purchased from J.T Baker (Deventer, Holland).

Figure 1A:
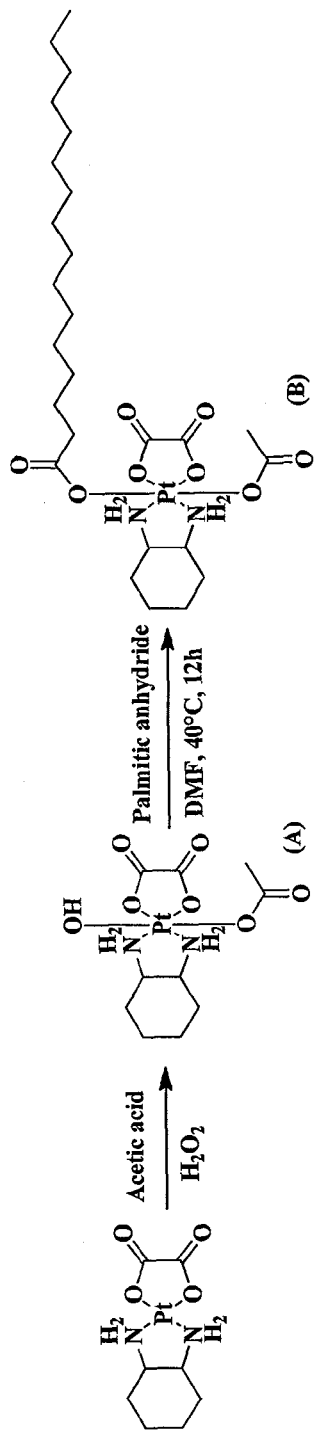
FIG. 1A is a description of the synthesis of OXA-PAL-ACT.
Figure 1B:
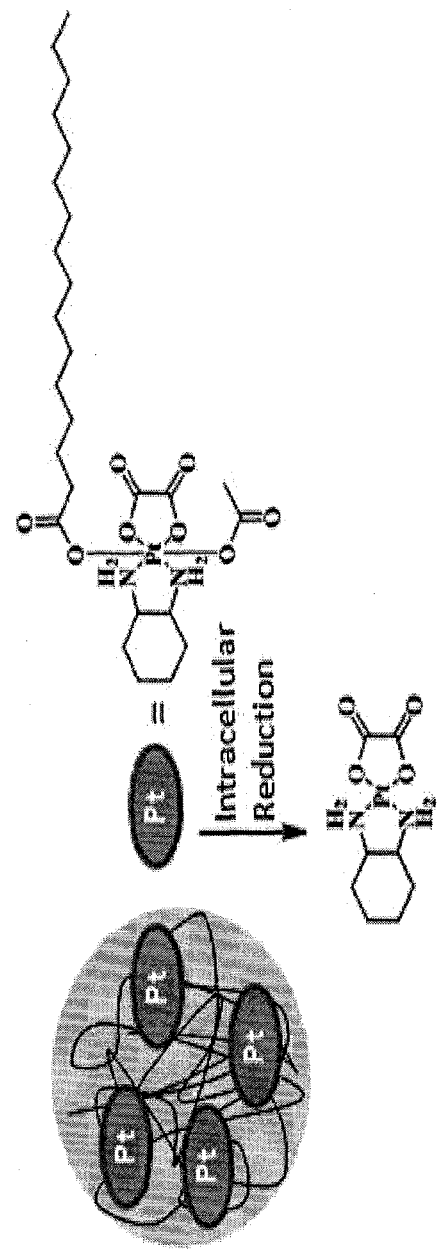
FIG. 1B shows a schematic representation of OXA-PAL-ACT NP construct. Chemical structure of the Pt(IV) prodrug intracellular reduction for the release of active oxaliplatin in human cancer cells.

Oxaliplatin Palmitate Acetate (OXA-PAL-ACT, Compound B of FIG. 1A) Synthesis
Synthesis of OXA-ACT-OH (A)

100 mg (0.252 mmol) of oxaliplatin was dissolved in 20 mL acetic acid and 1 μL of 30% $H_2O_2$ was added to it. The mixture was stirred at room temperature until all oxaliplatin completely dissolved (4-5 hours). Excess acetic acid was removed by vacuum evaporation and the resulting white solid was washed with diethyl ether and acetone and dried by vacuum evaporation. The compound was characterized by $^{195}$Pt NMR and $^1$H NMR. Yield: 51%.

Synthesis of OXA-PAL-ACT (B)
Synthesis of Palmitic Anhydride 500 mg Palmitic acid (1.95 mmol) was dissolved in 20 mL dichloromethane and 201.2 mg N,N'-Dicyclohexylcarbodiimide (0.5 eq., 0.975 mmol) was added to it. The reaction mixture was stirred at room temperature for 12 h. Progress of the reaction was monitored by TLC with ethyl acetate as the mobile phase. N,N'-Dicyclohexylurea that formed was filtered off from the reaction mixture and excess dichloromethane was removed by evaporation.

The white solid obtained after the removal of dichloromethane was re-dissolved in a small amount of dichloromethane and the N,N'-Dicyclohexylurea precipitated was filtered off. This process was repeated four times to remove N,N'-Dicyclohexylurea completely. Palmitic anhytride formed was characterized by 1H NMR. Yield: 89%.

Synthesis of OXA-PAL-ACT 50 mg OXA-ACT-OH (0.106 mmol) was dissolved in 5 mL DMF and 78.4 mg palmitic anhydride (1.5 eq., 0.159 mmol) was added to it. The reaction mixture was stirred at 400° C. for 12 h (overnight). Completion of reaction was checked by $^{195}$Pt NMR (disappearance of the peak at +1390 ppm and formation of a new peak at +1589 ppm). Unreacted anhydride was filtered off from the reaction mixture and DMF was removed by vacuum evaporation yielding a light yellowish solid stuck to the walls of round bottom flask.

Purification of OXA-PAL-ACT 1 mL methanol was added to the solid obtained after the evaporation of DMF and the mixture was shaken well (to dissolve the impurities and unreacted Pal-anhydride by methanol). The insoluble white precipitate was collected by centrifugation and washed twice with a small amount of methanol and dried in vacuum. Then, the product was further purified using HPLC. The compound obtained was characterized by $^{195}$Pt NMR and $^1$H NMR. Yield: 31%.

Log P Determination

The partition coefficient ($P_{ow}$) of OXA-PAL-ACT was determined in n-octanol and water by shake flask method, and Log P was calculated as follows:

$$\log P_{oct} = \log_{10} \frac{[Pt]_{oct}}{[Pt]_{aq}}$$

In Vitro Study
Cell Lines and Cell Incubation Conditions

The in vitro experiments were performed in cell lines of lung cancer (A549), prostate cancer (DU145 and PC-3), pancreatic cancer (BxPC-3) and ovarian cancer (SKOV-3 and OVCAR-8). A549, BxPC-3 and OVCAR-8 cells were grown in RPMI medium supplemented with 10% fetal bovine serum (Gibco), 1% L-glutamine, 100 U/ml penicillin, 100 ug/ml streptomycin and 0.13% w/w gentamycin. PC-3 cells were cultured in DMEM plus 10% fetal bovine serum, 1% L-glutamine, 100 U/ml penicillin, 100 μg/ml streptomycin and 1% pyrovate. DU145 cells were grown in RPMI1640 medium supplemented with 10% fetal bovine serum, 100 U/ml penicillin, and 100 ug/ml streptomycin. SKOV-3 cells were cultured McCoy's 5A medium supplemented with 10% fetal bovine serum, 100 U/ml penicillin, and 100 ug/ml streptomycin. The cell lines were maintained at 37° C. under 5% $CO_2$. All cell culture products were obtained from Biological Industries (Beit HaEmek, Israel). The drugs were dissolved in DMSO and were added to the appropriate medium. Drug concentrations were chosen in a range that would never expose cells to more than 0.5% DMSO i.e. for 50 μg/ml maximal concentration; 0.5 mg of OXA-PAL-ACT was dissolved in 50 μl DMSO and then added to 10 ml cell medium.

In Vitro Cytotoxicity Assay

To evaluate the efficacy of the various drugs, cells were seeded in a sterile, 24-well plate and incubated in the presence of the drug for 72 h/120 h at 37° C., 5% $CO_2$. The number of cells alive was quantified using (3-(4,5-dimethylthiazol-2-yl)-2,5 diphenyltetrazolium bromide) (MTT) assay. The cells were incubated for 2 h with MTT, DMSO was added to dissolve the crystals and the plates were measured at 540 nm. Viability (%) graphs were constructed relative to the control of every assay. The data were plotted in a graph, lines connected the points, and the values were determined from the interpolated graph.

Determination of Platinum Contents in the Cells

SKOV-3 and SKOV-3 LUC cells were seeded in triplicate 24 well plate ($50 \times 10^3$ cell/well), allowed to reach 80-90% confluence, and treated with oxaliplatin, OXA-PAL-ACT and OXA-PAL-ACT NPs 5 µg/ml, 15 µg/ml, 25 µg/ml for 24 h (37° C.).

Following incubation, the drug-containing medium was removed, and cells were rinsed twice with cold PBS, trypsinized and were centrifuged into a pellet (4400 rpm, 5 min). 500 µl of nitric acid was added to cell pellets, and overnight incubated at 70° C. The samples were prepared by dilution using 0.1% SDS and 1% nitric acid lysis solution, and analyzed for Pt content by ICP-MS. DNA was isolated and purified from cell lines with the DNeasy Blood and Tissue Kit (Qiagen).

Preparation of OXA-PAL-ACT Nanoparticles

The nanospheres of OXA-PAL-ACT were prepared by solvent deposition method (Nano-precipitation). Typically, 7 mg OXA-PAL-ACT, 14 mg PLGA 50 KDa, 7 mg lipoid E80 and 1.5 mg OCA were dissolved in 4 ml (1:20) ethanol/acetone mixture. The organic phase was added to 2.5 ml aqueous solution containing 0.1% w/v Solutol® HS 15. The suspension was stirred at 900 rpm over 15 min, and then concentrated by solvents' evaporation using air flow to a final volume of 2.5 ml, followed by centrifuge for 10 min at 4400 rpm.

Results and Discussion

OXA-PAL-ACT Synthesis and Characterization

Figure 2A:
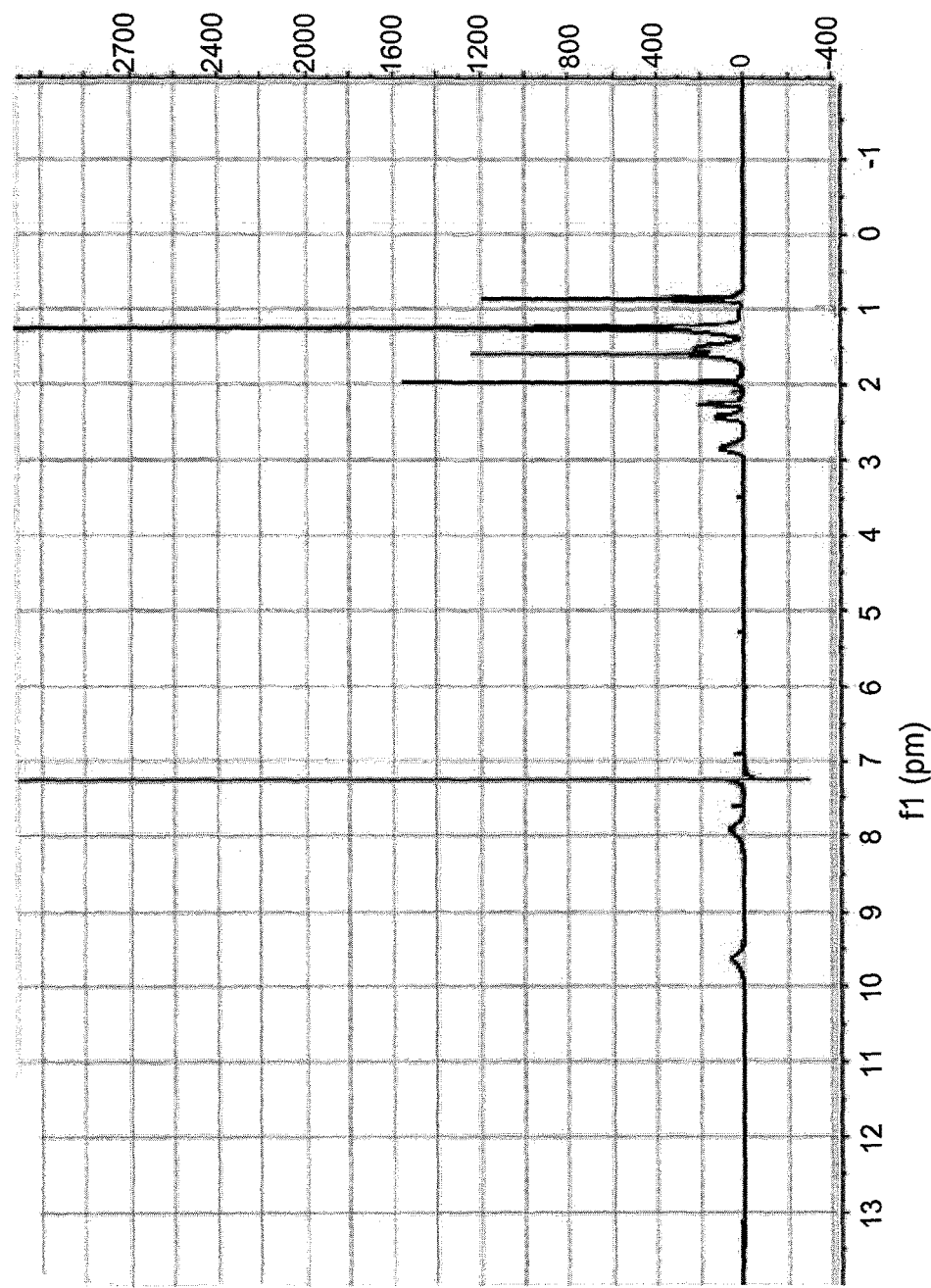
FIG. 2A shows OXA-PAL-ACT $^1$H-NMR spectrum.
Figure 2B:
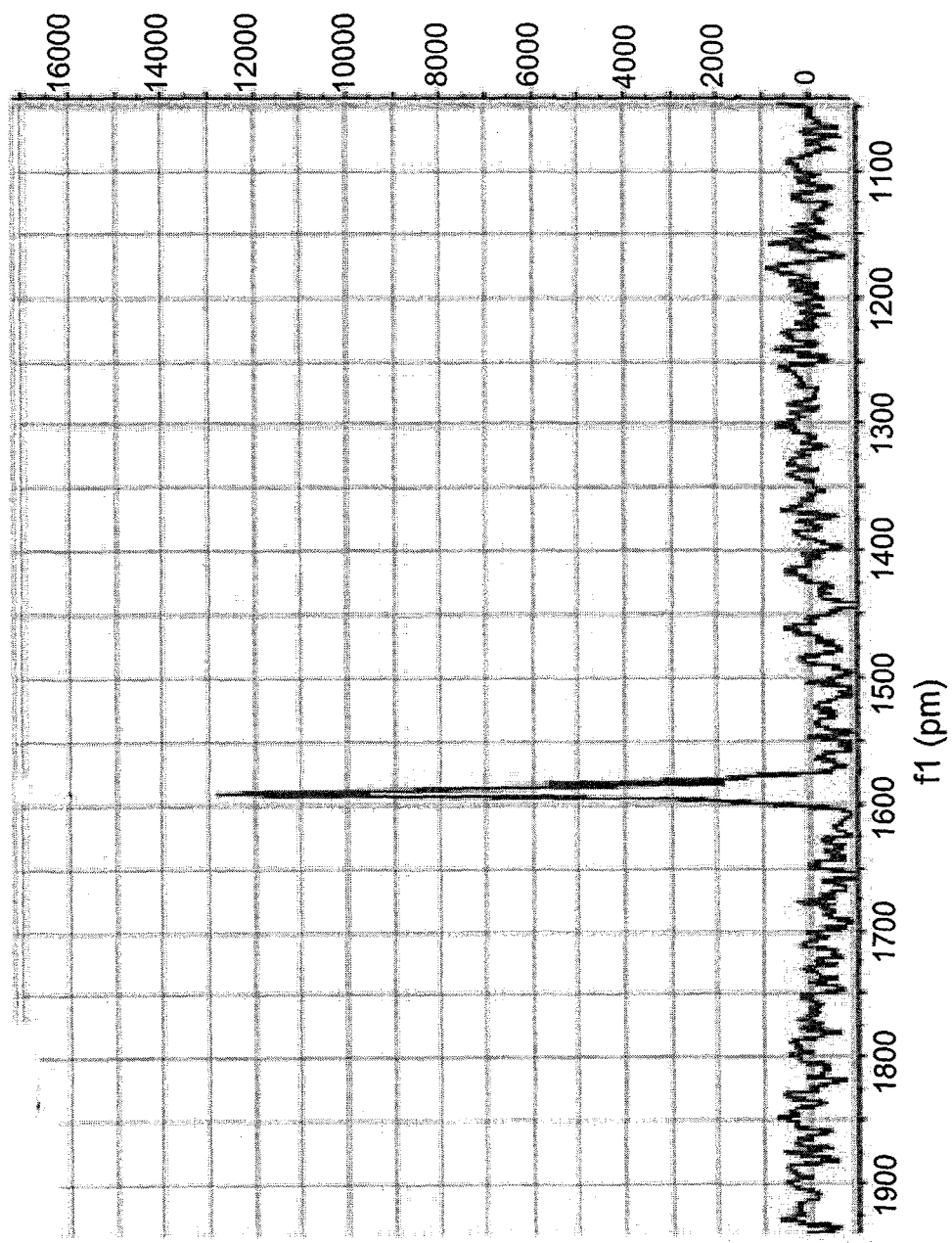
FIG. 2B shows OXA-PAL-ACT $^{195}$Pt-NMR spectrum: 1589 ppm.

OXA-PAL-ACT was identified using $^1$H-NMR, $^{195}$Pt-NMR, HPLC (FIGS. 2A-2B) and elemental analysis (Table 1).

TABLE 1

Elemental analysis values of OXA-PAL-ACT

| | C | H | N |
|---|---|---|---|
| Theoretical (%) | 43.87 | 6.80 | 3.94 |
| Analysis results (%) | 43.69 | 6.61 | 3.89 |

The observed Log P was 2.76±0.14 (n=5), while the calculated value (C Log P) was 8.57 (by Chemdraw software).

Preparation and Characterization of OXA-PAL-ACT NPs

After synthesizing OXA-PAL-ACT compound, spherical nanoparticles of it were obtained.

Figure 3A:
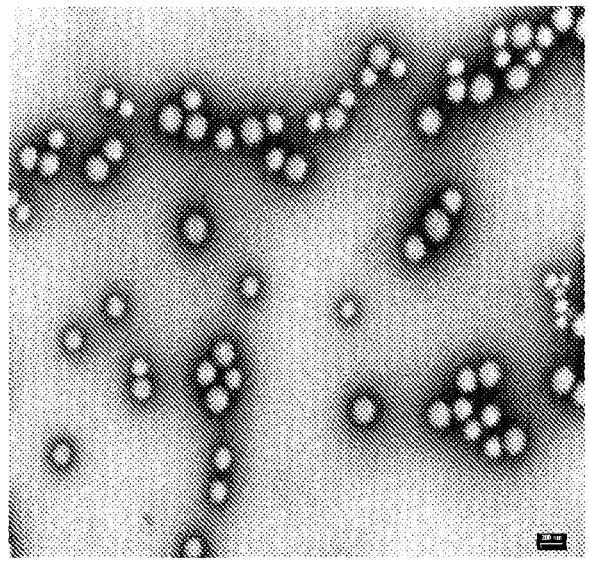
FIGS. 3A-C show TEM images of OXA-PAL-ACT NPs
Figure 3B:
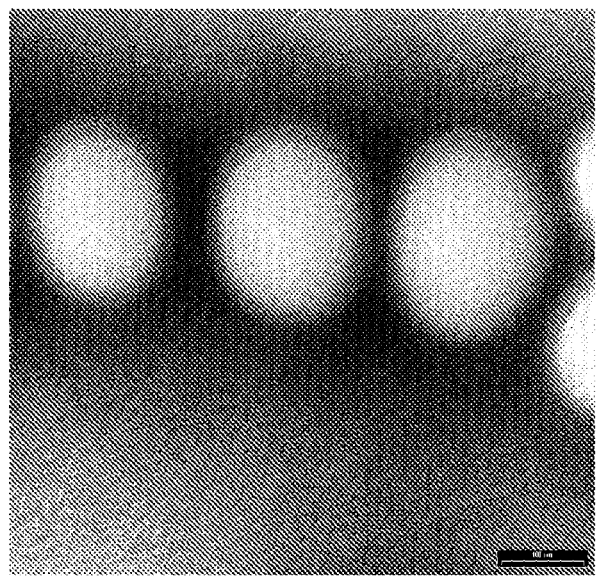
Figure 3C:
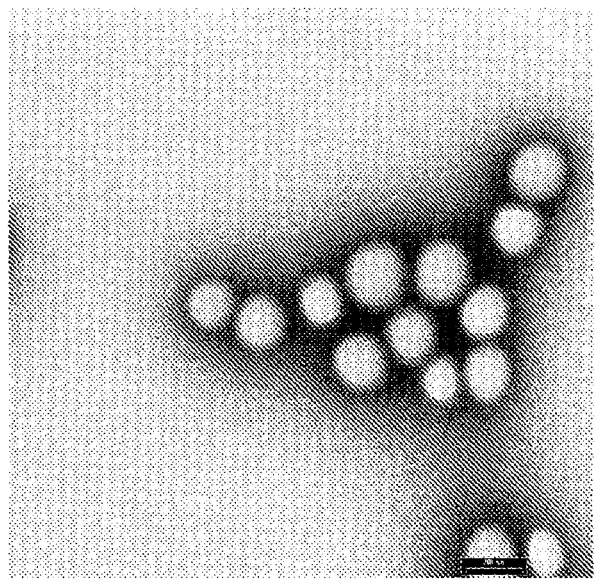
Figure 4A:
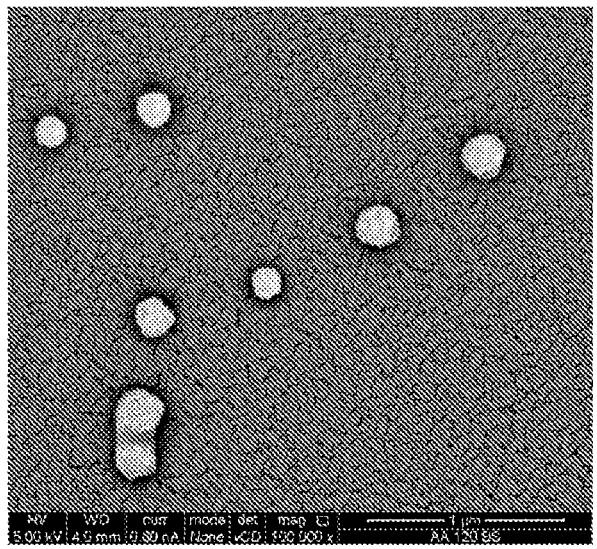
FIGS. 4A-B shows SEM images of OXA-PAL-ACT NPs.
Figure 4B:
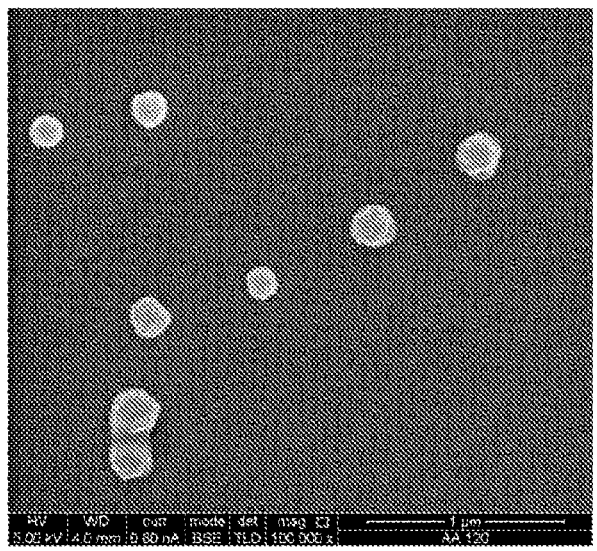
Figure 5:
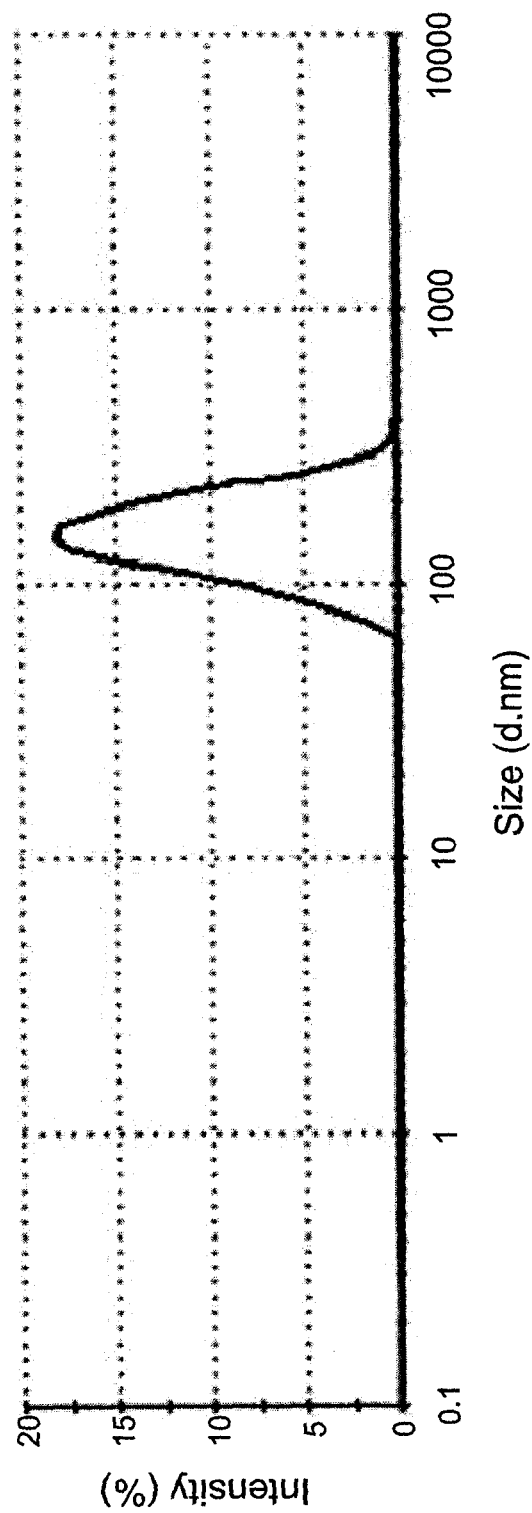
FIG. 5 shows representative measurement of the size of OXA-PAL-ACT NPs.

TEM, SEM and AFM were used to characterize the morphology and size of OXA-PAL-ACT NPs. Results showed that all of them assumed a spherical shape, their mean diameters ranged from 150 nm to 230 nm determined also by Malvern Zetasizer (Malvern Instruments, Malvern UK). The zeta potential values ranged from −45 mV to −50 mV. In addition, it was noted that high encapsulation yields of OXA-APL-ACT were obtained (>95%), and the incorporation of it in the NPs ranged from 21.5% to 22.7% w/w. (FIGS. 3-5 and Table 2)

TABLE 2

Physicochemical properties of OXA-PAL-ACT and blank NPs

| | Mean diameter (nm) | PDI value | Zeta potential (mV) | NP Content % w/w | Encapsulation Yield % | Final conc. (mg/ml) |
|---|---|---|---|---|---|---|
| OXA-PAL-ACT NPs | 146.3 ± 1.6 | 0.1 ± 0.01 | −49.3 ± 1.1 | 22.7 | 97.4 | 2.6 |
| Blank NPs | 180.4 ± 2.6 | 0.1 ± 0.01 | −48.6 ± 1.8 | — | — | — |
| Lyo-NPs | 197.1 ± 2.1 | 0.1 ± 0.02 | −51.7 ± 0.8 | 22.7 | 97.4 | 2.6 |

Figure 6A:
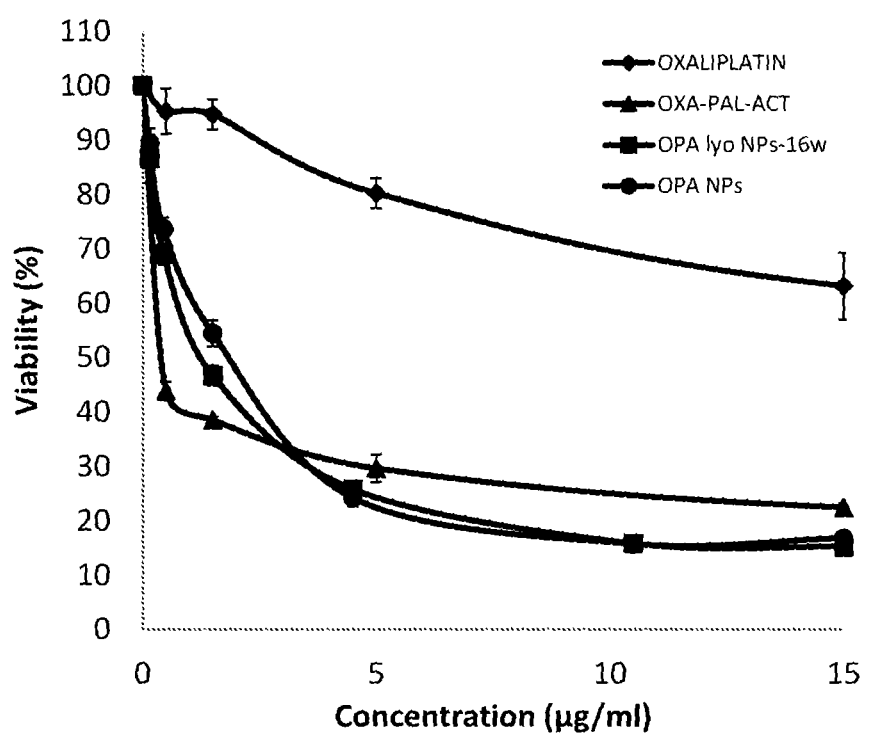
FIG. 6A shows in vitro evaluation of the cytotoxicity of OXA-PAL-ACT NPs in SKOV-3 cell line.
Figure 6B:
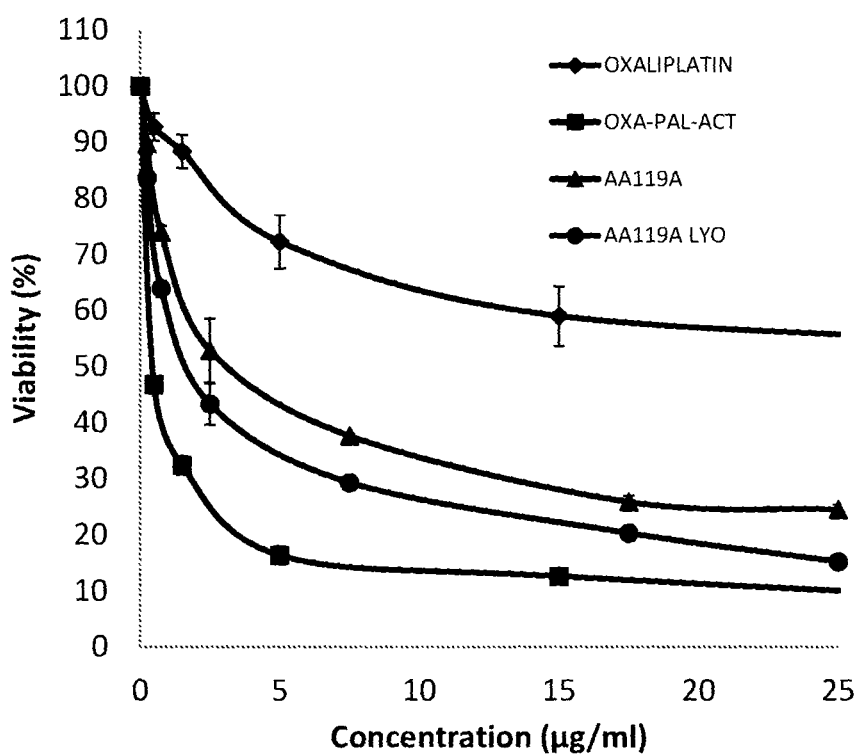
FIG. 6B shows in vitro evaluation of the cytotoxicity of OXA-PAL-ACT NPs in SKOV-3-luc cell line.
Figure 7A:
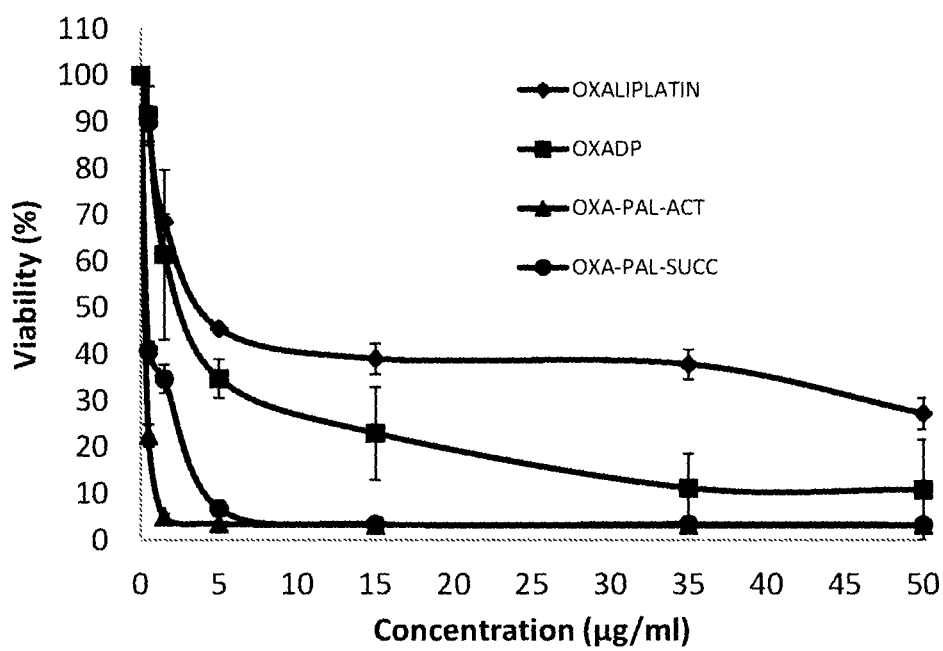
FIGS. 7A-B shows cytotoxic effect of oxaliplatin derivatives on PC-3 cell line: (A) entire concentration range; (B) 0-5 µg/ml.
Figure 7B:
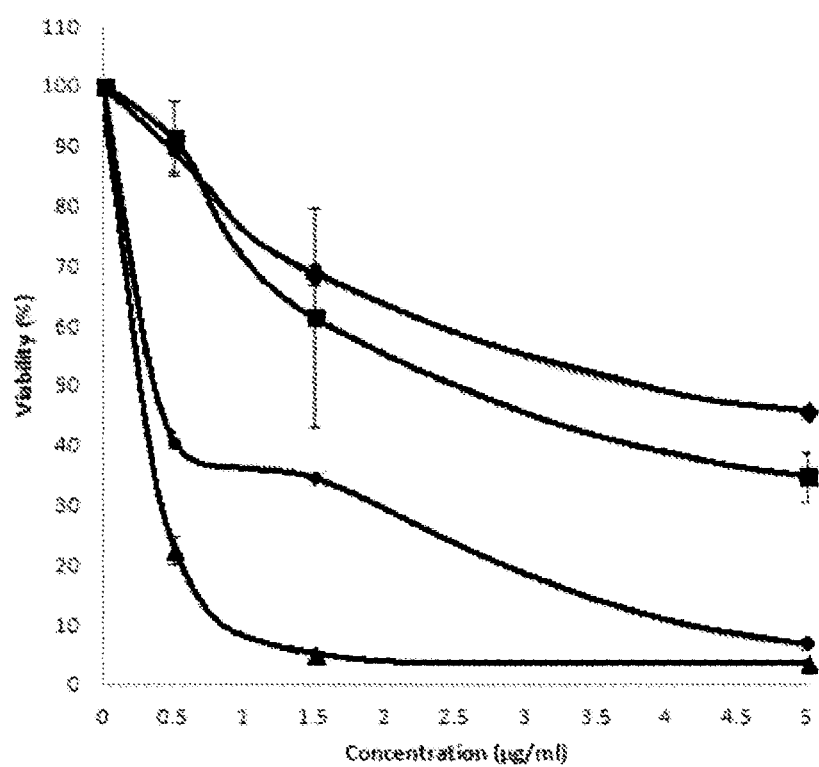
Figure 8A:
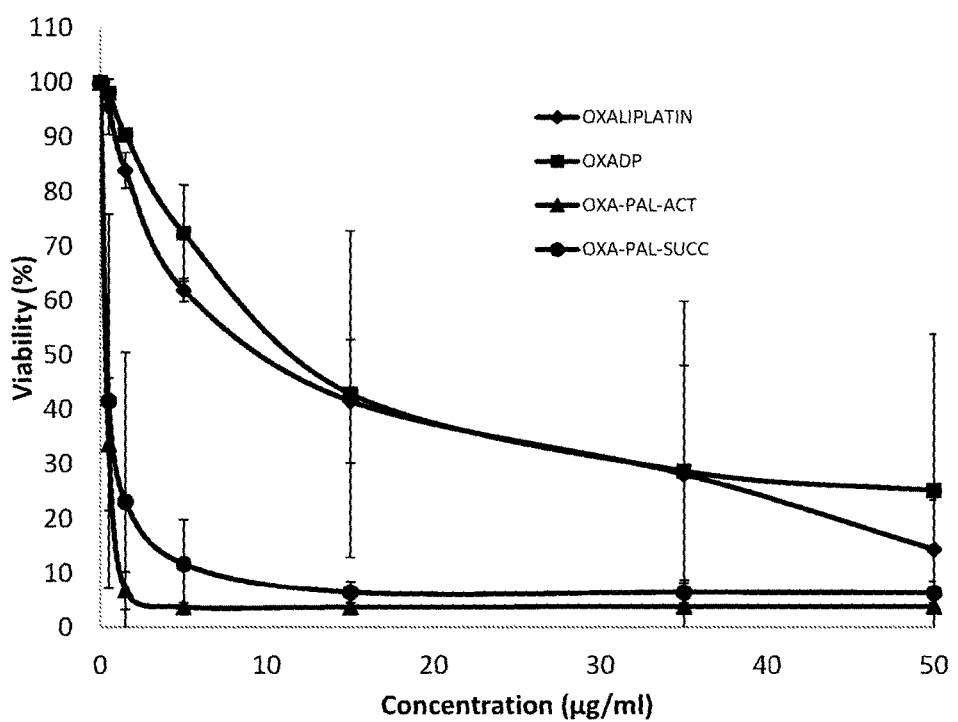
FIGS. 8A-D show (FIG. 8A) cytotoxic activity of oxaliplatin derivatives on PC-3 luc cell line monolayer representing prostate cancer.
Figure 8B:
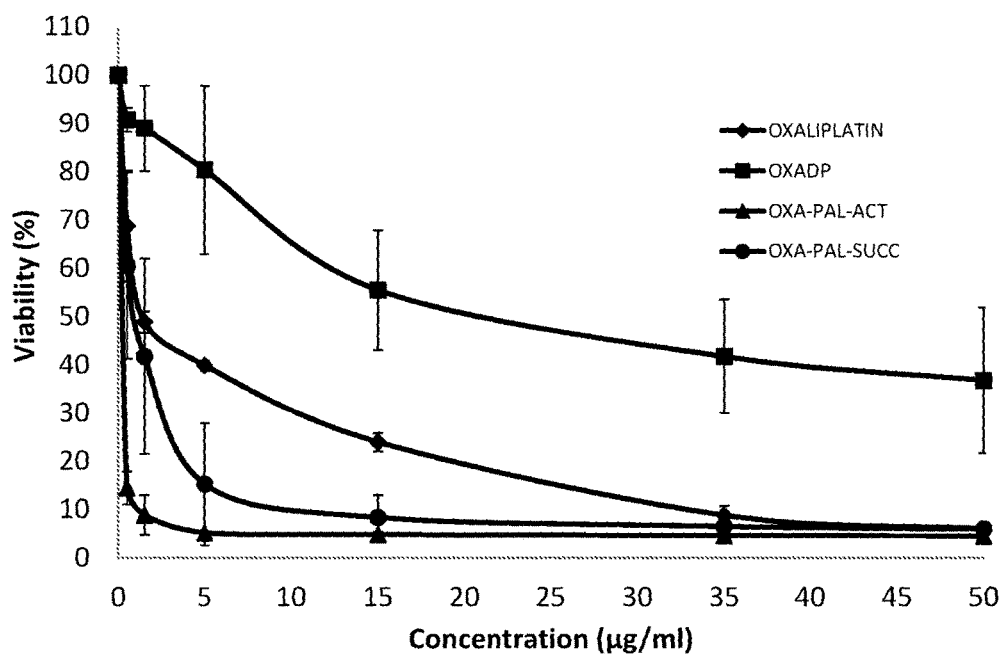
Figure 8C:
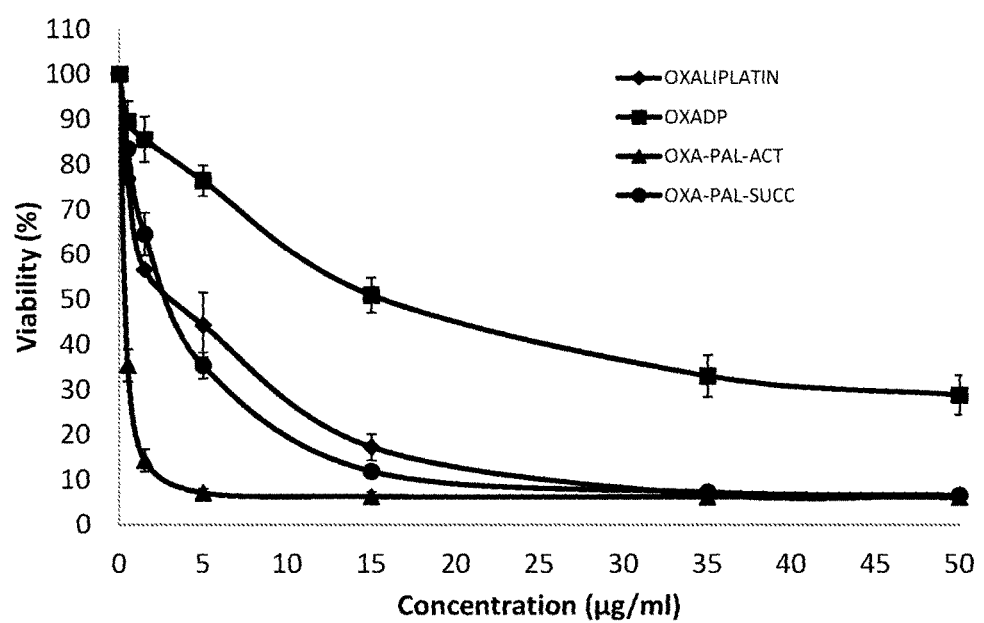
Figure 8D:
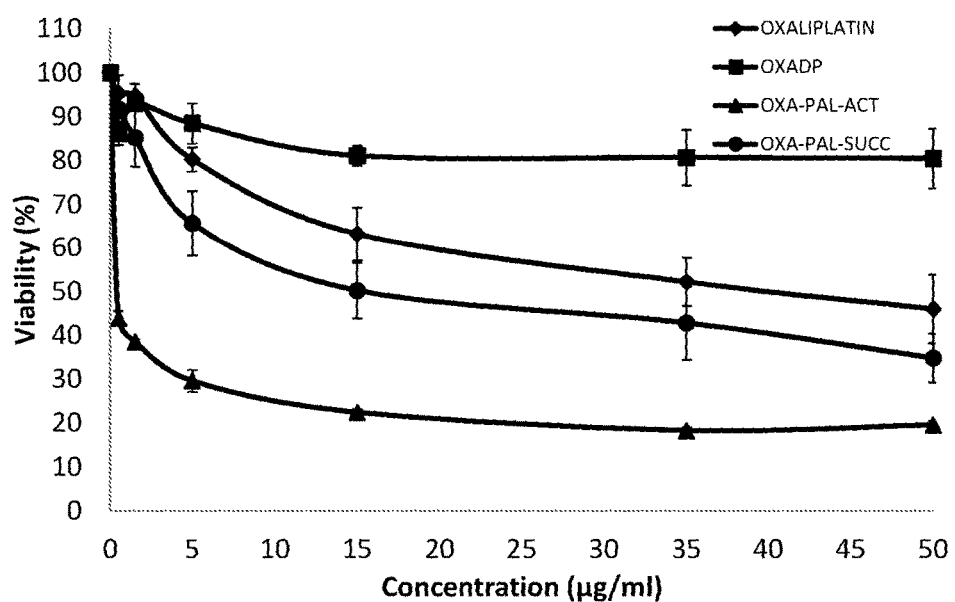
Figure 9:
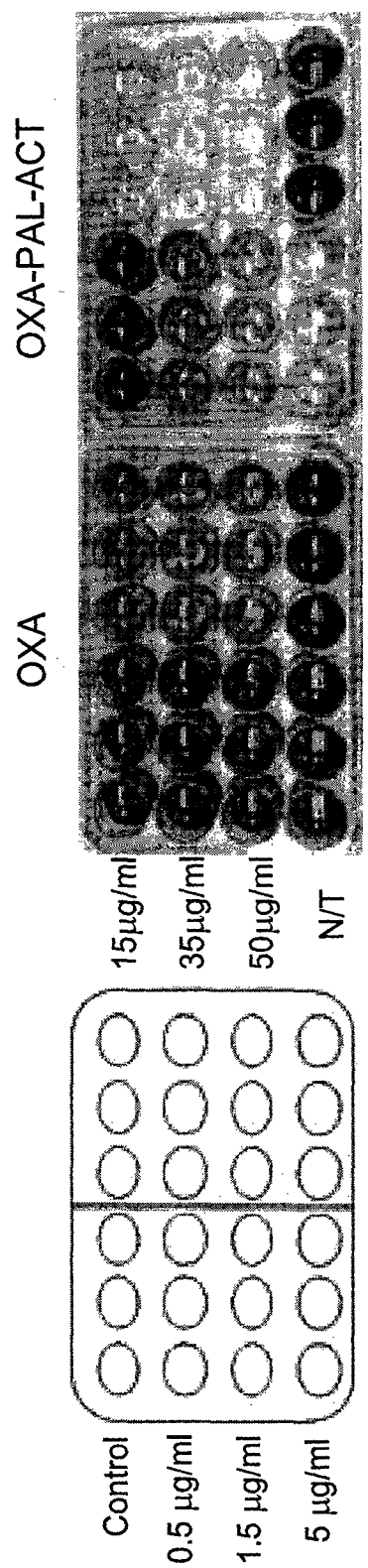
FIG. 9 shows MTT plates for oxaliplatin and OXA-PAL-ACT (SKOV-3 cell line).

In order to store larger batches of NPs, with the aim of pharmaceutical use, there was a need to develop a process for lyophilization of these NPs. After drug encapsulation, the NPs were freeze-dried using martin christ epsilon 2-6 d instrument. NPs when lyophilized with sucrose (5% w/v), as cryoprotectant, were physically stable. No significant changes in size, zeta potential or drug content was detected after freeze dried NPs kept at 4° C. for 1 month, besides, the in vitro cytotoxic activity of NPs was maintained (FIGS. 6A-6B).

Evaluation of OXA-PAL-ACT Biological Properties

As can be seen in FIGS. 7-11 and Tables 3A-3B, the $IC_{50}$ values of oxaliplatin derivatives were determined in various cancer cell lines following 120 h treatment. OXA-PAL-ACT has unique potency against cancer cells, with greater efficacy than oxaliplatin, moreover, it has broad spectrum of activity against various cancer cells that are typically resistant to platinum therapy.

TABLE 3A

Summary of IC$_{50}$ values of oxaliplatin derivatives in various cancer cell lines following 120 h treatment

| | PC-3 | PC-3 LUC | BXPC-3 | OVCAR-8 | SKOV-3 | A2780 | A2780-cisR |
|---|---|---|---|---|---|---|---|
| Oxaliplatin μg/ml | 3.63 ± 0.15 | 11 ± 3.60 | 1.35 ± 0.35 | 3.75 ± 1.77 | 32.5 ± 3.54 | 0.31 | 1.63 ± 0.11 |
| OXADP μg/ml | 2.20 ± 1.21 | 21.35 ± 19.30 | 24.07 ± 12.96 | 16 ± 3.12 | N.D* | | |
| OXA-PAL-ACT μg/ml | 0.25 ± 0.01 | 0.33 ± 0.08 | 0.25 ± 0.01 | 0.33 ± 0.03 | 0.39 ± 0.02 | 0.26 | 0.24 |
| OXA-PAL-SUCC μg/ml | 0.35 ± 0.01 | 0.78 ± 0.88 | 1.23 ± 1.18 | 2.83 ± 0.38 | 20.67 ± 15.88 | | |

*N.D—Not Determined (The IC$_{50}$ value is higher than maximal tested concentration-50 μg/ml).
** The data are from three independent experiments.

TABLE 3B

Summary of IC$_{50}$ values of oxaliplatin derivatives in various cancer cell lines following 120 h treatment

| | A549 | HCT-15 | A498 | A375 |
|---|---|---|---|---|
| Cisplatin μg/ml | 8.35 | 11.32 | 17.53 | 3.75 ± 1.77 |
| OXA-PAL-ACT μg/ml | 0.34 | 0.43 | 0.20 | 0.16 |
| OXA-PAL-SUCC μg/ml | 0.45 | 0.35 | 0.24 | 0.19 |

* N.D—Not Determined (The IC$_{50}$ value is higher than maximal tested concentration-50 μg/ml).
** The data are from three independent experiments.

Figure 10A:
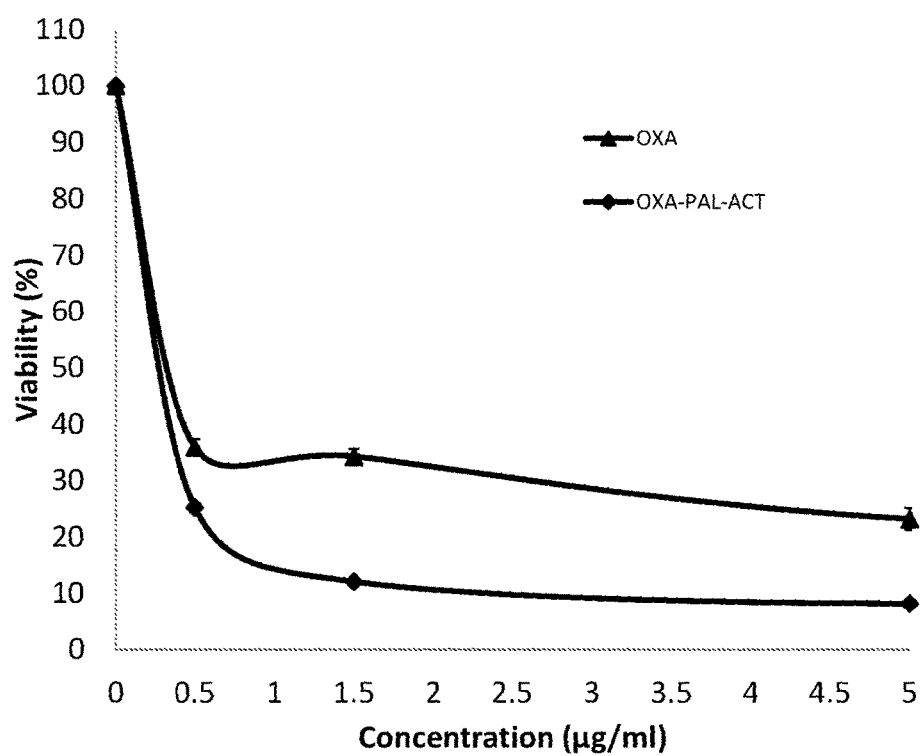
FIGS. 10A-B show cytotoxic effect of oxaliplatin and OXA-PAL-ACT on (FIG. 10A) A2780-cisR and (FIG. 10B) A2780 cell lines representing ovarian cancer.
Figure 10B:
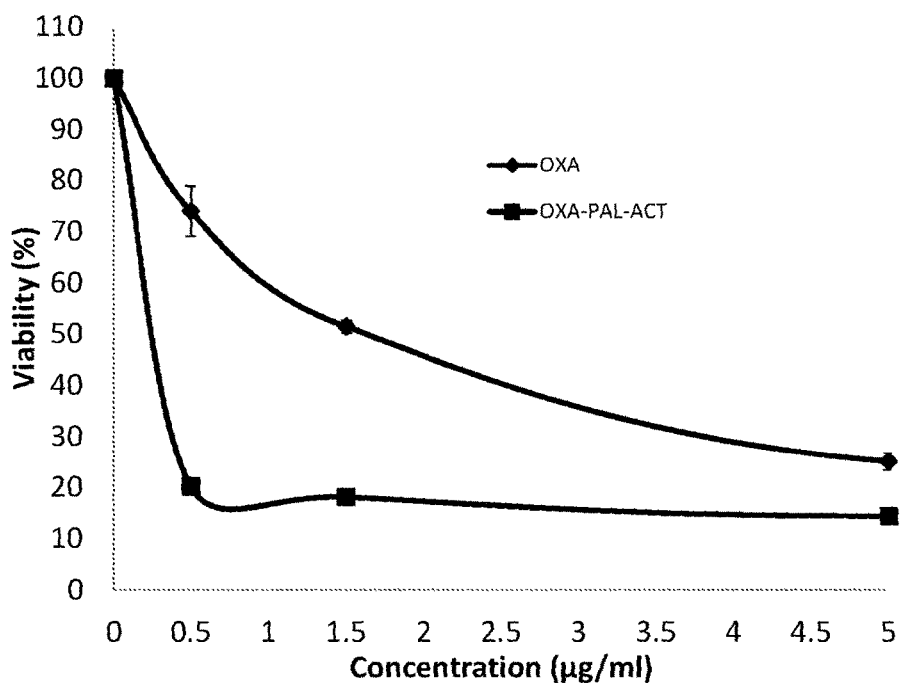
Figure 11:
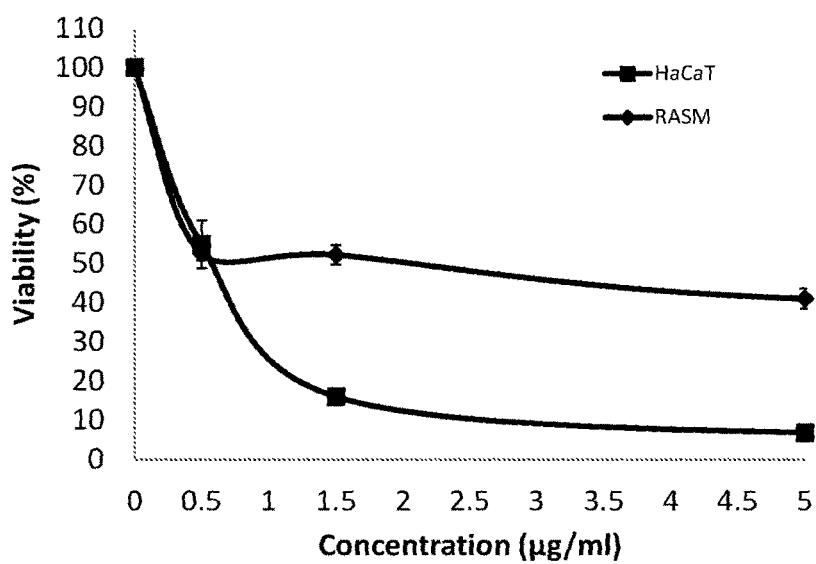
FIG. 11 shows Cytotoxic effect of OXA-PAL-ACT on non-cancer cell lines. The therapeutic ratio in HaCaT and RASM was higher than 1.8 and 2, respectively. HaCaT cell line monolayer representing human keratinocytes, RASM line monolayer representing Rat Aortic Smooth Muscle cells.

As shown in FIG. 10, the activity of OXA and OXA-PAL-ACT against two ovarian cancer cell lines was determined. A2780 is the parent line to the cisplatin resistant cell line A2780-cisR, as a result, the resistance factor was calculated from IC$_{50}$ values of dose-response curves. The resistance factors of OXA and OXA-PAL-ACT were 5.2 and 1, respectively, which indicates that OXA-PAL-ACT may be effective against cancer types that are typically resistant to platinum therapy.

Figure 12A:
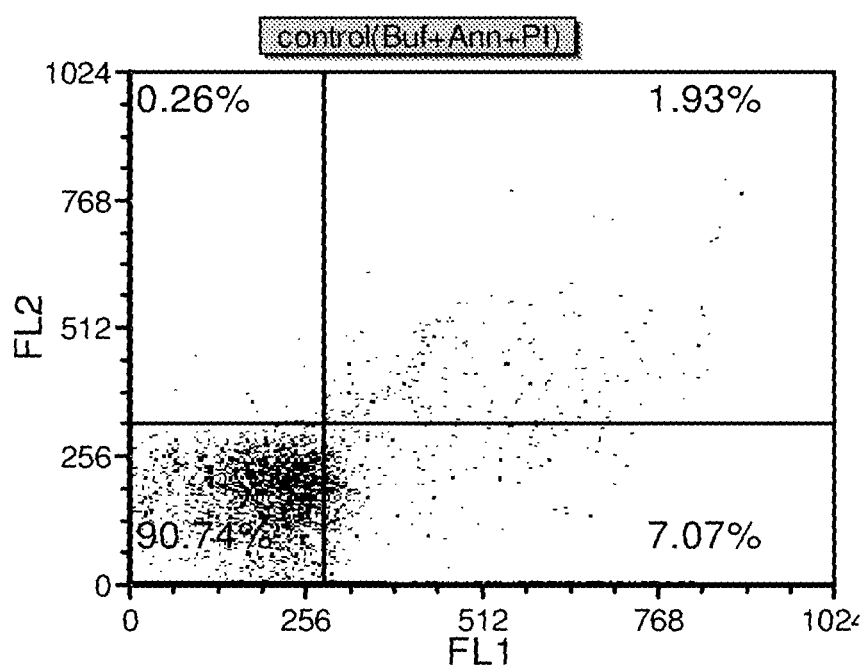
FIGS. 12A-C show SKOV-3 cell apoptosis. Apoptotic-cell death in SKOV-3 cells was evaluated by flow cytometry analysis using Annexin V and propidium iodide (PI) double staining. Cells were treated with 5 µg/ml (FIG. 12B) and 50 µg/ml (FIG. 12C) OXA-PAL-ACT for 24 h. Control is shown in FIG. 12A. The apoptotic cells are [annexin V(+) PI(+) and annexin V(+) PI(−) cells].
Figure 12B:
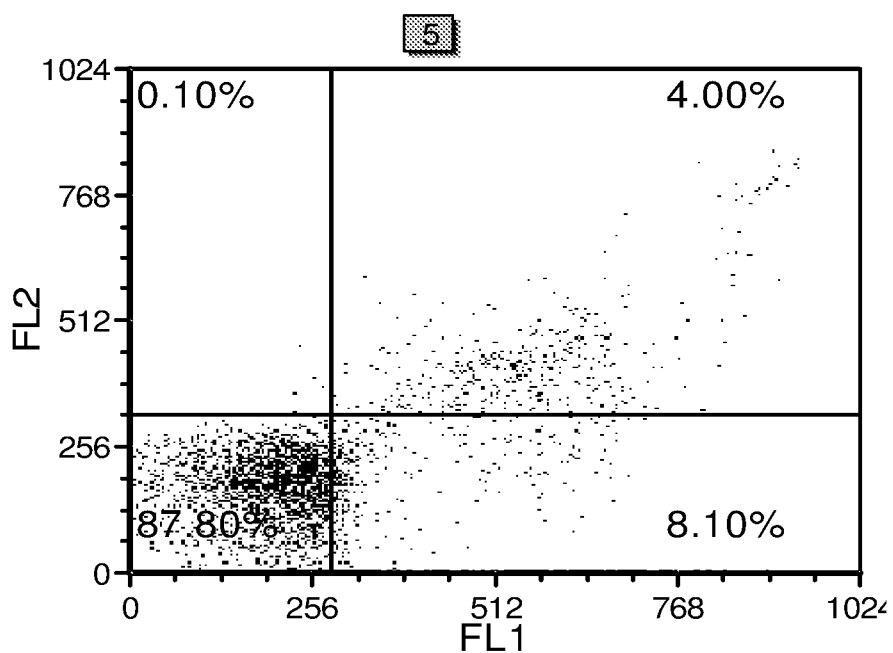
Figure 12C:
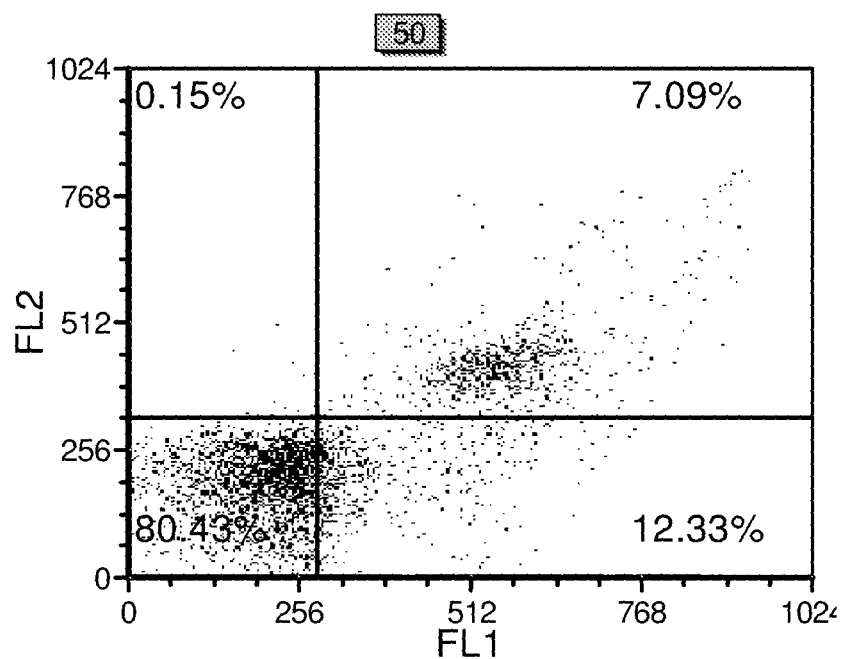

Apoptotic-cell death in SKOV-3 cells was evaluated by flow cytometry analysis using Annexin V and propidium iodide (PI) double staining. Cells were treated with 5 μg/ml and 50 μg/ml OXA-PAL-ACT for 24 h. The results are provided in FIG. 12.

Figure 13A:
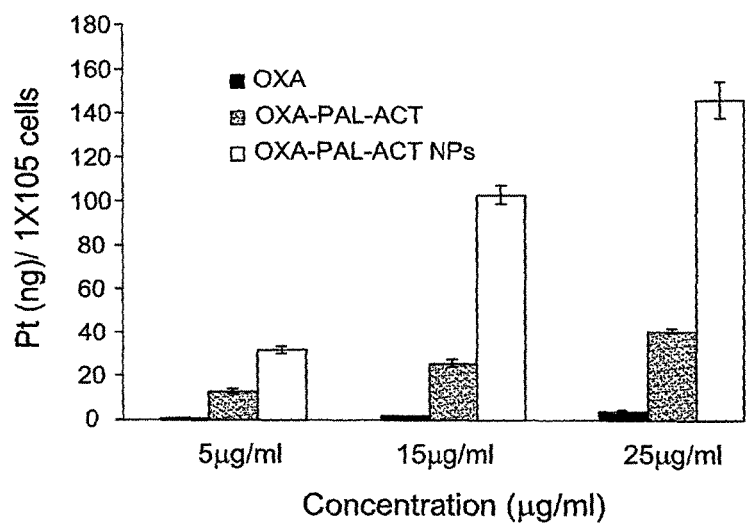
FIGS. 13A-B show whole-cell Pt accumulation (Cellular uptake) following incubation with varying drug concentrations following 24 h exposure in SKOV-3-luc cells as measured by ICP-MS. Values are mean±standard deviation (n=3)
Figure 13B:
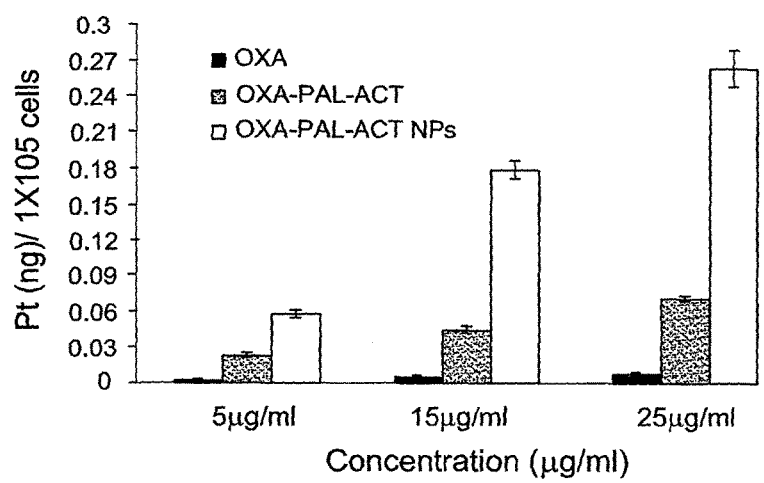
Figure 14A:
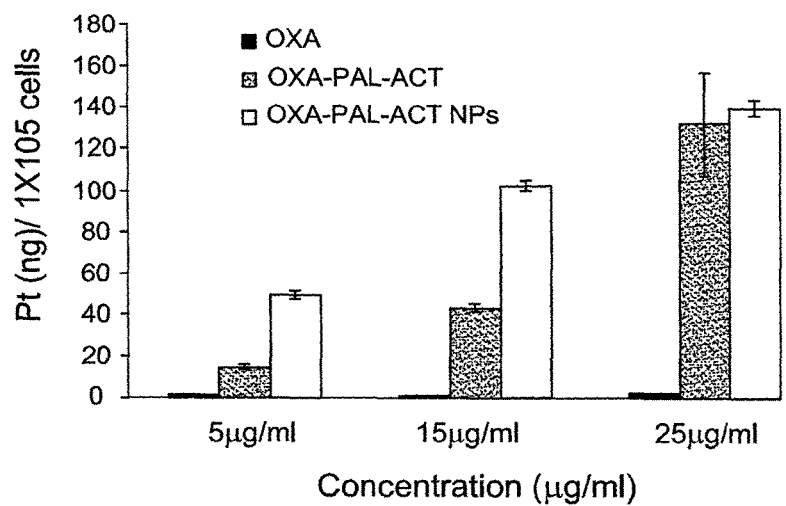
FIGS. 14A-B show whole-cell Pt accumulation (Cellular uptake) following incubation with varying drug concentrations following 24 h exposure in SKOV-3 cells as measured by ICP-MS. Values are mean±standard deviation (n=3)
Figure 14B:
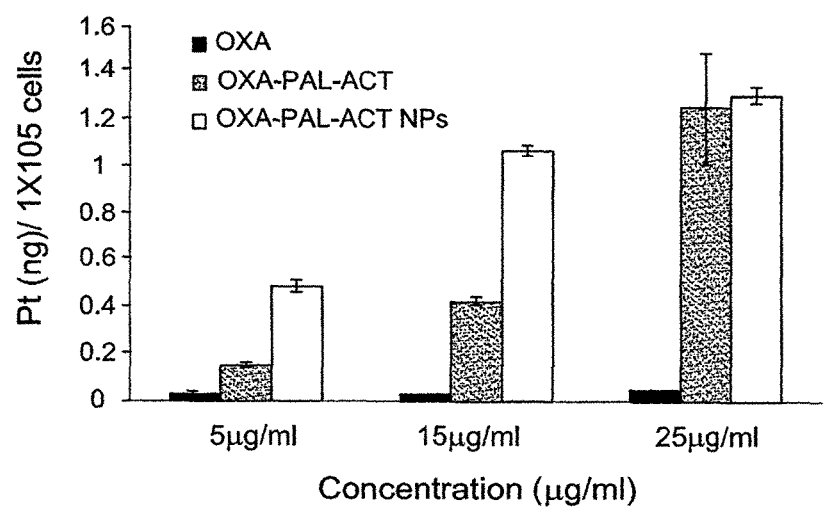

Cellular accumulation of platinum is a key step in cellular platinum drug pharmacology. To examine relative accumulation of OXA-PAL-ACT in cancer cells, the total Pt content was measured in SKOV-3 and SKOV-3-luc cells following their exposure to oxaliplatin, OXA-PAL-ACT or OXA-PAL-ACT NPs at varying drug concentrations. The data, normalized either to the total cellular protein or 1×10$^5$ cells, are presented in FIGS. 13-14. The cellular accumulation of OXA-PAL-ACT and OXA-PAL-ACT NPs was substantially higher compared to that of oxaliplatin.

Figure 15:
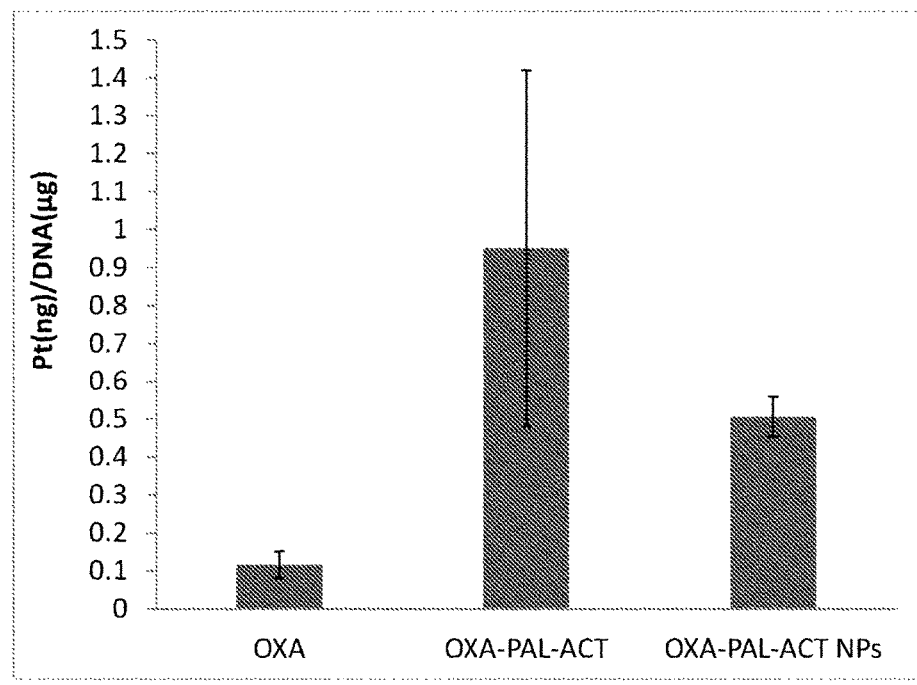
FIG. 15 shows the extent of DNA platination following 24 h exposure in SKOV-3 cells as measured by ICP-MS. Values are mean±standard deviation (n=7). Statistical analysis was performed using SPSS and revealed that the observed difference in DNA platination values was significant ($P<0.01$, ANOVA and $P<0.01$, Kruskal-Wallis Test). Post hoc analysis showed that there is significant difference between OXA and OXA-PAL-ACT solution/NPs (**$P<0.01$, Tukey).

Analysis of the extent of nucleus DNA platination measured after 24 h exposure of SKOV-3 cells to 25 μg/ml of oxaliplatin, OXA-PAL-ACT or OXA-PAL-ACT NPs, shown in FIG. 15 indicates higher DNA-platination of OXA-PAL-ACT in comparison to oxaliplatin. It is generally accepted that DNA damage induced by binding of platinum drugs is largely responsible for their cytotoxic properties. Thus, the higher DNA platination not surprisingly manifested as an increased cytotoxicity of OXA-PAL-ACT compared to the free oxaliplatin against SKOV-3 human ovarian cancer cell line.

Cellular Uptake of NPs in SKOV-3 Cells by CLSM

Cellular uptake and localization of NPs was already observed 15 min following incubation and was most evident at 6 h. The nucleus was stained by DAPI whereas the NPs fluorescently labeled using Rhodamine were easily visualized within the cytoplasm. Indeed, increased cytoplasmic accumulation of NPs was observed as a function of dilution (1:100 versus 1:200) and at 6 h compared to 1, 3 time intervals, with a more pronounced perinuclear and nuclear localization pattern.

Ovarian Carcinoma Mouse Model

For induction of an ovarian carcinoma mouse model, 5-6 weeks-old severe combined immunodeficiency (SCID) mice, divided into 4 groups, were injected with 2×10$^6$ SKOV-3 luc cells directly into intraperitoneal cavity (i.p.). The cells were suspended in 100 μl PBS.

Dosage Regimen

Treatment was administered once a week by i.v. injection, 4 treatments in total. The treatment groups comprised free oxaliplatin at dose of 5 mg/kg body weight, OXA-PAL-ACT at dose of 15 mg/kg body weight, injection solution (vehicle) as control, and OXA-PAL-ACT NPs 15 mg/kg. All treatments were given in an identical treatment regimen. For tumor validation and tumor growth follow up, bioluminescent imaging was performed every 7 days using a CCCD camera (IVIS, Caliper Life Sciences, Xenogen Corporation). D-luciferin was injected intraperitoneally and mice were anesthetized by 3% isoflurane Animals were placed onto black paper in the IVIS imaging box and imaged dorsally and ventrally. Total luminescence (dorsal and ventral) was recorded in radiance units (photons/sec/cm$^2$). 30 days following cells injection and validation of tumor inoculation, animals were divided into four groups with equal average radiance values.

Figure 16A:
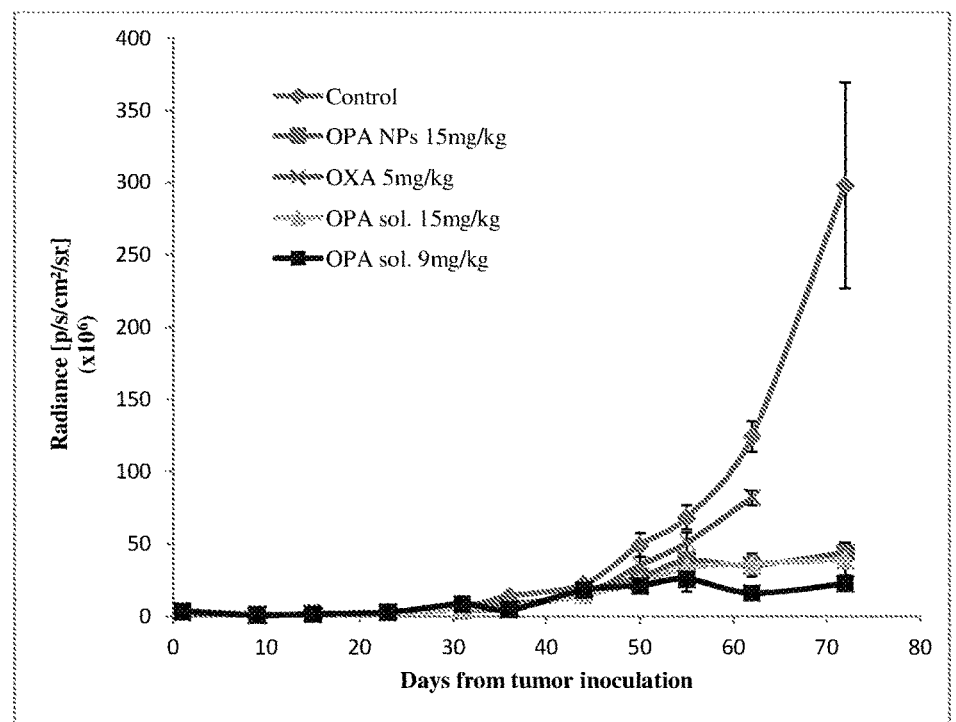
FIG. 16A shows longitudinal detection and quantification of SKOV-3 luc tumor growth in live mice by the bioluminescent luciferase imaging assay. Statistical analysis was performed using SPSS and revealed that the observed difference was significant (one way ANOVA $P<0.01$). Post hoc analysis using Dunnett test (2-sided) showed that there is significant difference between the control group and each OPA treatment group ($P<0.01$).
Figure 16B:
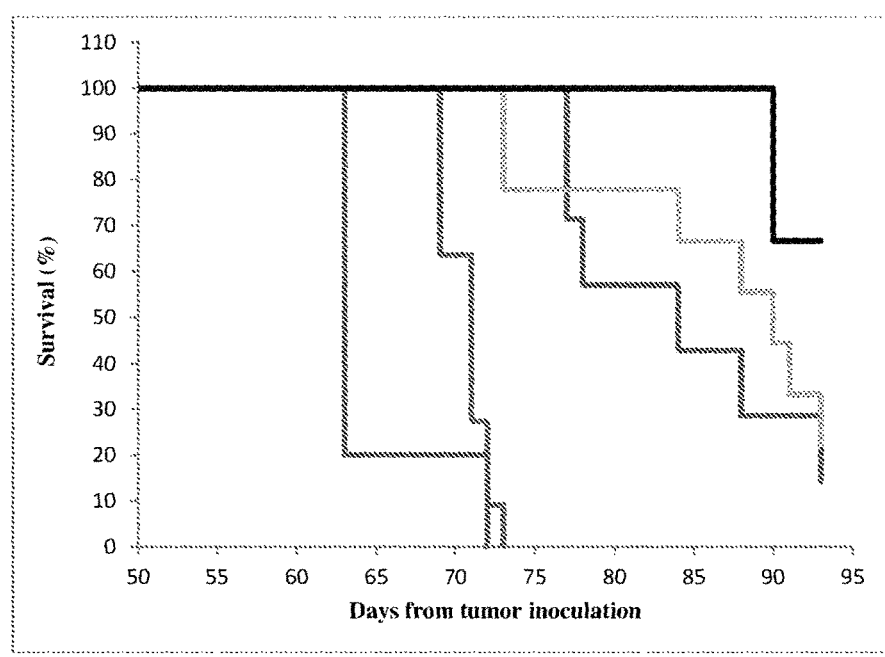
FIG. 16B shows Kaplan-Meier survival curve from tumor cells injection day until death (according to the approved ethical committee euthanasia requirements. The study was terminated on the 93$^{rd}$ day).
Figure 17:
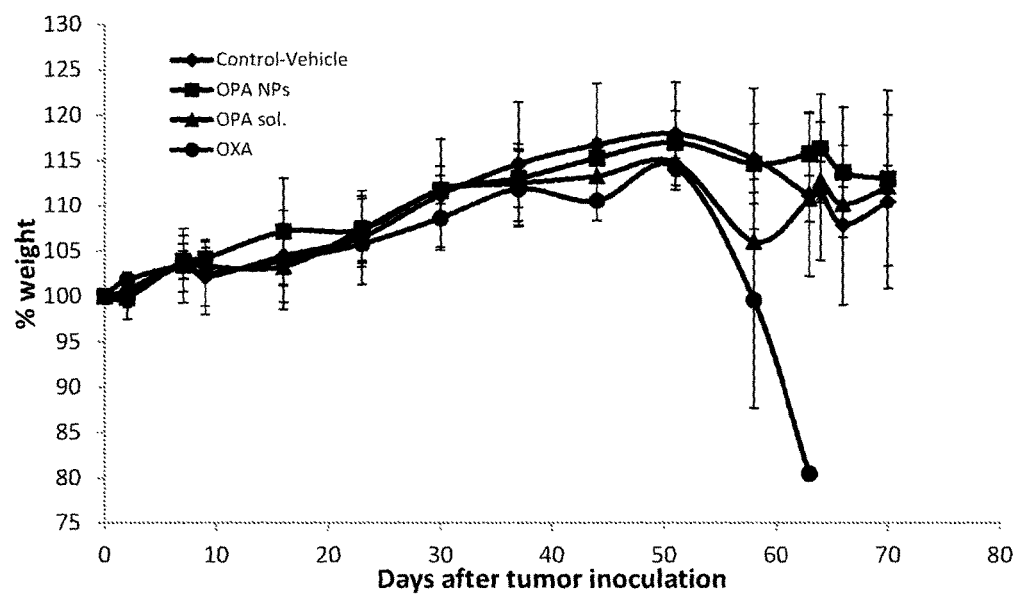
FIG. 17 shows body weight follow-up beginning from tumor inoculation (day 0) through the entire study period until euthanasia. Changes were recorded as a percent of the initial body weight observed one day prior to tumor cells injection (100% at day 0). Results are presented as mean±SD, until the last surviving animal (according to the approved ethical committee euthanasia requirements).
Figure 18A:
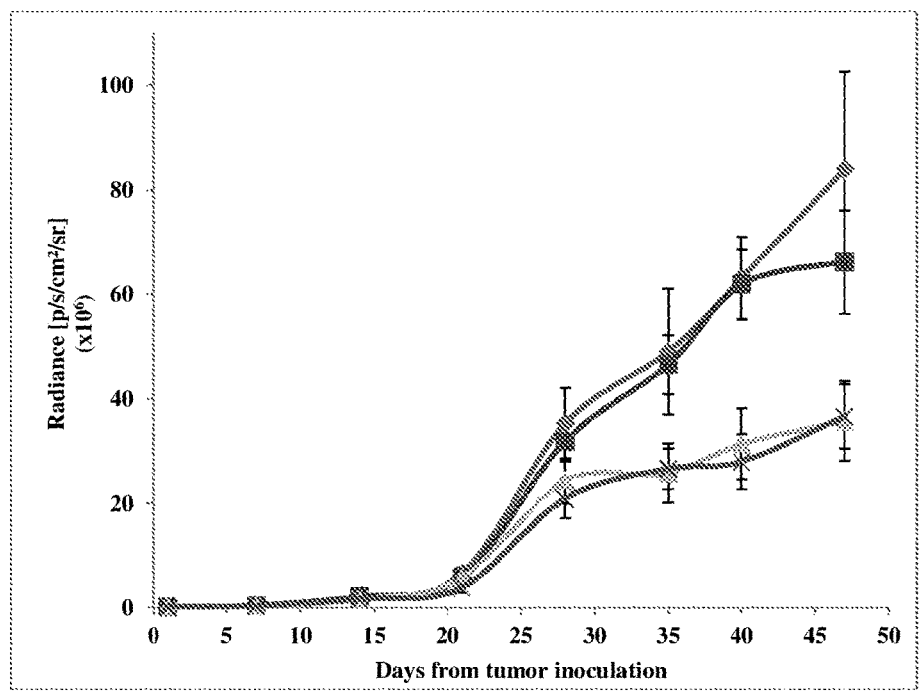
FIG. 18A Longitudinal detection and quantification of BxPC-3-luc2 tumor growth from cells injection (day 0 up to 47) in SCID-bg live mice (n=7-9) by the bioluminescent luciferase imaging assay. Results are presented as mean±SEM. Statistical analysis was performed using SPSS and revealed that the observed difference between the groups is significant (one way ANOVA **$P<0.01$).
Figure 18B:
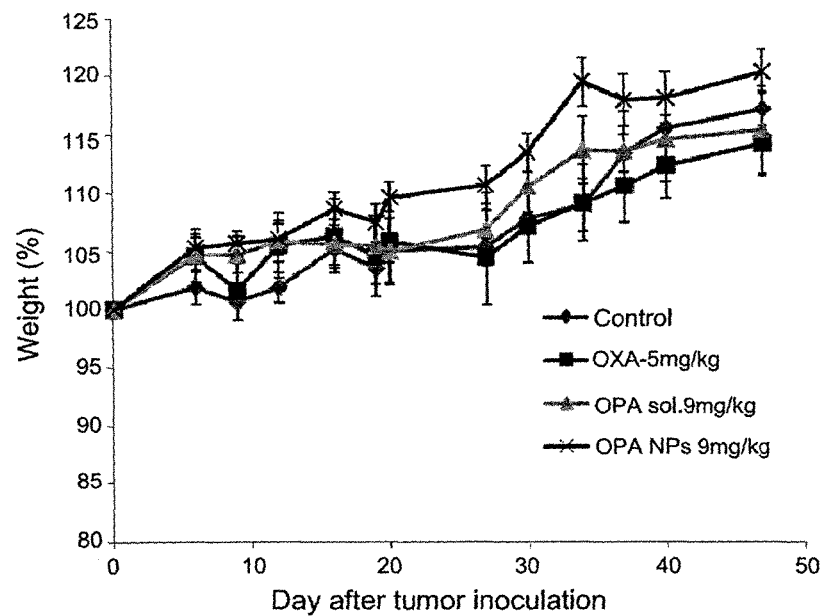
FIG. 18B shows body weight follow-up beginning from tumor inoculation (day 0) through the entire study period until euthanasia. Results are presented as mean±SD, until the last surviving animal (according to the approved ethical committee euthanasia requirements).

As can be seen in FIG. 16A, treatment started from day 30. The maximum tolerated dose of OXA solution was 5 mg/kg whereas the maximal tolerated dose of OXA-PAL-ACT in solution was 15 mg/kg due to the vehicle's toxicity. It is of note that OXA-PAL-ACT incorporated in NPs was well tolerated at the dose of 30 mg/kg. It could be observed that from day 60 both OXA-PAL-ACT in solution and in NPs were more efficient that OXA. There was no difference between OXA-PAL-ACT sol and NPs at the same dose as depicted in FIG. 16B. In addition, in FIG. 17, the body weight variation over time is presented. While OXA was toxic as reflected by the marked weight reduction starting close to day 50 from cell inoculation, the remaining formulation including OXA-PAL-ACT sol and NPs did not reduce the animal weight similarly to the control-vehicle and some gain was also noted showing that the OXA-PAL-ACT formulations were well tolerated visually. These results are very encouraging and open novel therapeutic opportunities to the clinicians in the future offering a new therapeutic arsenal to fight life threatening cancer diseases.

Pancreatic Carcinoma 5-6 weeks-old SCID mice were inoculated subcutaneously with $2 \times 10^6$ BxPC-3-luc cells. 7 days following tumor inoculation, mice were divided into four groups with equal average radiance values.

Treatment was administered once a week by i.v. injection (tail), 4 treatments in total.

The antiproliferative activities of the novel compound (free and incorporated in NPs) and OXA were determined in HCT 116-luc2 (human colorectal cancer) and BxPc-3-luc2 (human pancreatic cancer) cell lines by the MTT assay. The resulting 50% growth inhibitory concentration ($IC_{50}$) values are presented in Table 4.

TABLE 4

$IC_{50}$ values of OXA, OXA-PAL-ACT (OPA), and OPA NPs in two cancer cell lines.

| | $IC_{50}$ (μM) | | |
|---|---|---|---|
| Cell line | OXA | OPA | OPA NPs |
| HCT 116-luc2 | 2.30 ± 1.08 | 0.37 ± 0.02 | 0.40 ± 0.02 |
| BxPc-3-luc2 | 62.67 ± 2.52 | 0.31 ± 0.09 | 0.31 ± 0.01 |

Pancreatic tumors were induced by subcutaneous injection of the luciferase-transfected pancreas adenocarcinoma cells, BxPc-3-luc2, to SCID-bg mice. Tumor development and progression was validated by bioluminescent imaging. On the eighth day following tumor cells injection, a four-treatment cycle (intravenous route) was initiated (once a week). OPA and OPA NPs were equally and significantly more efficient in pancreatic tumor growth inhibition compared to OXA and the control. Furthermore, there was no difference between the control and OXA which did not show any efficacy in this specific cell line.

Colon Cancer Model 5-6 weeks-old SCID mice were inoculated subcutaneously with $1 \times 10^6$ HCT-116-luc2 cells. 1 day following tumor inoculation, treatment was initiated. Treatment was administered once every fourth day by i.v. injection (tail), 4 treatments in total.

Figure 19:
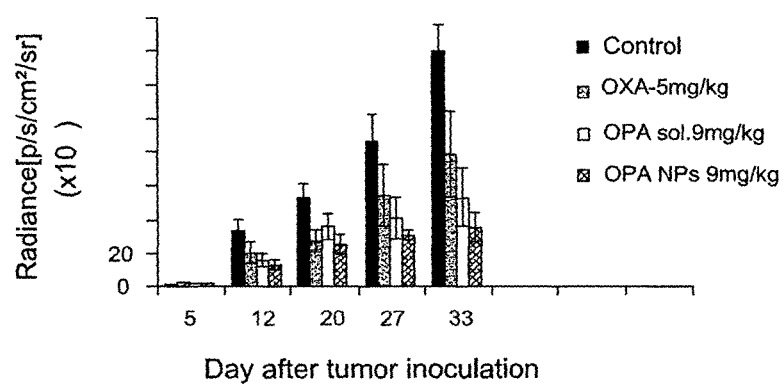
FIG. 19 Longitudinal detection and quantification of HCT-116-luc2 tumor growth from cells injection (day 0 up to 33) in SCID-bg live mice (n=9-10) by the bioluminescent luciferase imaging assay. Results are presented as mean±SEM. Statistical analysis was performed using SPSS and revealed that the observed difference between the groups is significant (one way ANOVA **P<0.01).

FIG. 19 shows Longitudinal detection and quantification of HCT-116-luc2 tumor growth from cells injection (day 0 up to 33) in SCID-bg live mice (n=9-10) by the bioluminescent luciferase imaging assay. Results are presented as mean±SEM. Statistical analysis was performed using SPSS and revealed that the observed difference between the groups is significant (one way ANOVA **P<0.01). In fact equivalent doses were infected since 9 mg/kg OPA is equivalent to 5 mg/kg OXA. It can be noted that the tumor growths progressively and markedly with the Control over time whereas the most pronounced inhibitory effect is elicited by the OPA NPs at time interval of 33 days from the tumor inoculation. The results of OPA NPs are significantly more efficient in inhibition of the tumor than the inhibition effect elicited by OXA at equivalent dose. However there is no significant efficacy difference between the OPA solution and the OPA NPs or between the OPA solution and the OXA solution (FIG. 19).

Comparative Study

The partition coefficient of the new Pt compounds was determined in n-octanol and water by shake flask method. The resulting log P values are reported in Table 5. As expected, the measured log P values of the new derivatives were greater than OXA, indicating their intrinsic lipophilic character.

TABLE 5

$^{195}$Pt NMR shifts, experimentally measured logP, and reduction potentials measured by cyclic voltammetry of Pt compounds.

| Compound | $^{195}$Pt shift (DMF) | Measured logP | Ep (V)[a] |
|---|---|---|---|
| OXA | −2012 | −0.45 | — |
| OPA | +1589 | 2.06 | −0.54 ± 0.02 |
| OPS | +1585 | 2.07 | −0.60 ± 0.01 |
| ODP | +1589 | 3.49 | −0.53 ± 0.02 |
| CDDP | −2168 | −1.39 | — |

[a]versus Ag/AgCl.

Evaluation of OXA-PAL-ACT (OPA) Biological Properties

The antiproliferative activities of the novel compounds and oxaliplatin were determined in PC-3, PC-3-luc (human prostate cancer), BxPC-3 (human pancreatic cancer), OVCAR-8, SKOV-3 (human ovarian cancer), CT-26-luc (murine colorectal cancer) cell lines by the MTT assay. The cells were treated continuously for 120 h. The resulting 50% growth inhibitory concentration ($IC_{50}$) values are summarized in Table 6. OPA showed unique potency against different cancer cell lines, with greater cytotoxicity than OXA. Furthermore, it has broad spectrum of activity against cancer cells that are typically resistant to platinum-based compounds.

TABLE 6

$IC_{50}$ values of OXA derivatives in various cancer cell lines following 120 h incubation.

| | $IC_{50}$ (μM)* | | | | | |
|---|---|---|---|---|---|---|
| Compound | PC-3 | PC-3-luc | BxPC-3 | OVCAR-8 | SKOV-3 | CT-26-luc |
| OXA | 9.16 ± 0.37 | 27.7 ± 9.05 | 3.38 ± 0.87 | 9.44 ± 4.44 | 58.26 ± 6.34 | 5.60 ± 0.60 |
| ODP | 2.42 ± 1.33 | 23.51 ± 21.24 | 26.49 ± 14.27 | 17.61 ± 3.43 | >55 | >55 |
| OPA | 0.35 ± 0.01 | 0.46 ± 0.11 | 0.35 ± 0.01 | 0.46 ± 0.03 | 0.54 ± 0.03 | 0.62 ± 0.24 |
| OPS | 0.45 ± 0.01 | 1.01 ± 1.13 | 1.59 ± 1.52 | 3.67 ± 0.49 | 26.85 ± 20.62 | 4.43 ± 0.93 |

*Values are the means ± standard deviations obtained from three independent experiments.

The activity of OXA and OPA against a pair of cisplatin sensitive and resistant ovarian cancer cell lines, A2780 and A2780-cisR, was determined as a function of the concentration. A2780cisR is resistant to cisplatin through a combination of decreased uptake, enhanced DNA repair/tolerance, and elevated reduced glutathione (GSH) levels.

The resistance factor is the ratio of $IC_{50}$ value in resistant cell line to that in the parent cell line (Table 7), which indicates that OPA can overcome acquired resistance to cisplatin and may be effective against cancer types that are typically resistant to platinum therapy.

TABLE 7

$IC_{50}$ (μM) values and RF for compounds against A2780, A2780-cisR

| Compound | $IC_{50}$ (μM)[a] | | F[b] |
|---|---|---|---|
| | A2780 | A2780-cisR | |
| OXA | 0.78 ± 0.02 | 4.1 ± 0.25 | 5.21 |
| ODP | 7.5 ± 0.5 | >55 | >7.3 |
| OPA | 0.36 ± 0.01 | 0.34 ± 0.01 | 0.93 |
| OPS | 0.46 ± 0.01 | 1.9 ± 0.2 | 4.13 |
| CDDP | 0.94 ± 0.04 | 14.6 ± 1.44 | 15.53 |

[a]$IC_{50}$ values are drug concentrations required for 50% cell death and are the means ± SD of three independent experiments.
[b]RF standing for resistance factor is the ratio of $IC_{50}$ value in resistant cell line to that in the parent cell line.

It should be emphasized that irrespective of the cell line, OPA was always more cytotoxic and efficient than ODP oxaliplatin dipalmitate suggesting that the value of the Log P is not the only parameter affecting the cytotoxicity effect but also the amphiphilicity of the molecule does influence the cytotoxicity effect. A certain log P value is needed apparently close to the value of 2 to allow a good and rapid permeability of the cancerous cells as reflected by the results described in Tables 6 and 7.

Cellular uptake and localization of NPs was already observed 15 min following incubation and was most evident at 6 h. The nucleus was stained by DAPI whereas the NPs fluorescently labeled using PE Lissamine Rhodamine B were easily visualized within the cytoplasm. Indeed, increased cytoplasmic accumulation of NPs was observed as a function of dilution (1:100 versus 1:200) and at 6 h compared to 1, 3 h time intervals, with a more pronounced perinuclear and nuclear localization pattern.

The invention claimed is:

1. A compound of formula (I), or a salt form thereof:

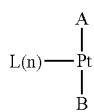
(I)

wherein
Pt is a platinum atom;
A is a $C_8$-$C_{22}$ fatty acid associated with the Pt atom via an oxygen atom of the fatty acid;
B is a $C_2$-$C_7$ fatty acid associated with the Pt atom via an oxygen atom of the fatty acid;
provided that each of A and B is not $C_6$-$C_9$ branched alkyl fatty acid;
L is a ligand atom or group of atoms selected from the group consisting of a halide atom, substituted or unsubstituted amine —$NR_1R_2$, —NH, ligand L1:

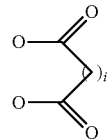
(L1)

wherein i is an integer between 0 and 5 and the ligand L1 associates to the Pt via the oxygen atoms,
ligand L2:

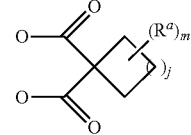
(L2)

wherein j is an integer between 0 and 2, m is an integer between 0 and 6, and $R^a$ is selected from the group consisting of hydrogen, substituted or unsubstituted alkyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, substituted or unsubstituted heteroaryl, substituted or unsubstituted heterocyclyl, substituted or unsubstituted alkenyl, substituted or unsubstituted alkynyl, halogen, substituted or unsubstituted —$NR_1R_2$, substituted or unsubstituted —$OR_3$, substituted or unsubstituted —$SR_4$, substituted or unsubstituted —$S(O)R_5$, substituted or unsubstituted alkylene-COOH, substituted or unsubstituted ester, OH, —SH, and —NH, phenyl and hydroxyl, and the ligand L2 associates to the Pt via the oxygen atoms,
ligand L3:

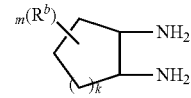
(L3)

wherein k is an integer between 0 and 2, m is an integer between 0 and 6, and $R^b$ is selected from the group consisting of hydrogen, substituted or unsubstituted alkyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, substituted or unsubstituted heteroaryl, substituted or unsubstituted heterocyclyl, substituted or unsubstituted alkenyl, substituted or unsubstituted alkynyl, halogen, substituted or unsubstituted —$NR_1R_2$, substituted or unsubstituted —$OR_3$, substituted or unsubstituted —$SR_4$, substituted or unsubstituted —$S(O)R_5$, substituted or unsubstituted alkylene-COOH, substituted or unsubstituted ester, OH, —SH, and —NH, phenyl, hydroxyl, and the ligand L3 associates to the Pt via the amine moieties, ligand L4:

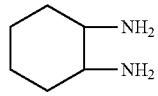

wherein the ligand L4 associates to the Pt via the amine moieties, ligand L5:

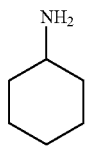

wherein the ligand L5 associates to the Pt via the amine moiety; and n is the number of ligand moieties, being 1, 2, 3, or 4, wherein, in each of L1-L5, $R_1$ and $R_2$ are each independently selected from the group consisting of hydrogen, alkyl, alkenyl, alkenyl, cycloalkyl, cycloalkenyl, cycloalkynyl, aryl, heteroaryl, heterocyclyl, halide, —C(O)NR$_6$R$_7$, sulfinyl, ester, and carbonyl, or $R_1$ and $R_2$ form a cyclic structure with the N atom they are bonded to, each of $R_3$, $R_4$, and $R_5$ is independently selected from hydrogen, alkyl, alkenyl, alkenyl, cycloalkyl, cycloalkenyl, cycloalkynyl, aryl, heteroaryl, heterocyclyl, halide, sulfinyl, ester, and carbonyl, and $R_6$ and $R_7$ are each independently selected from the group consisting of hydrogen, alkyl, alkenyl, alkenyl, cycloalkyl, cycloalkenyl, cycloalkynyl, aryl, heteroaryl, heterocyclyl, halide, sulfinyl, ester, carbonyl, —OH, —SH and NH, wherein at least one ligand L is bound to the platinum atom via at least one heteroatom selected from nitrogen, oxygen and sulfur.

2. The compound according to claim 1, wherein at least one of the bonds between the platinum atom and the heteroatoms are covalent and the other remaining bonds are coordinative bonds.

3. The compound according to claim 1 being of formula (Va) or (IXa):

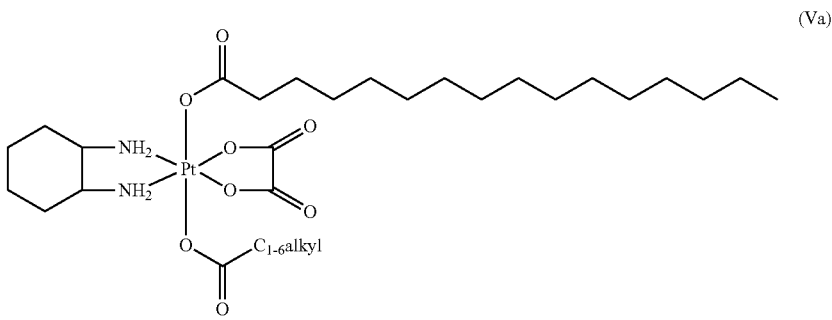

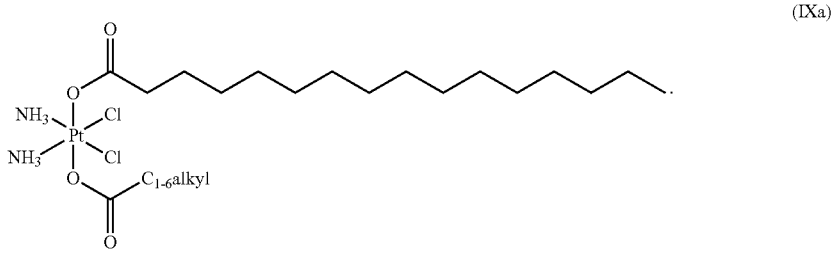

4. The compound according to claim 3, wherein said $C_{1-6}$ alkyl is methyl.

5. The compound according to claim 3, wherein the compound is oxaliplatin palmitate acetate.

6. The compound according to claim 1 being Oxaliplatin palmitate acetate.

7. A composition comprising a compound according to claim 1.

8. The composition according to claim 7, being a pharmaceutical composition.

* * * * *